(12) United States Patent
Wayne et al.

(10) Patent No.: US 12,159,221 B2
(45) Date of Patent: Dec. 3, 2024

(54) TRAINING AN UNSUPERVISED MEMORY-BASED PREDICTION SYSTEM TO LEARN COMPRESSED REPRESENTATIONS OF AN ENVIRONMENT

(71) Applicant: DeepMind Technologies Limited, London (GB)

(72) Inventors: Gregory Duncan Wayne, London (GB); Chia-Chun Hung, London (GB); David Antony Amos, London (GB); Mehdi Mirza Mohammadi, London (GB); Arun Ahuja, London (GB); Timothy Paul Lillicrap, London (GB)

(73) Assignee: DeepMind Technologies Limited, London (GB)

( * ) Notice: Subject to any disclaimer, the term of this patent is extended or adjusted under 35 U.S.C. 154(b) by 646 days.

(21) Appl. No.: 16/766,945

(22) PCT Filed: Mar. 11, 2019

(86) PCT No.: PCT/EP2019/055950
§ 371 (c)(1),
(2) Date: May 26, 2020

(87) PCT Pub. No.: WO2019/170905
PCT Pub. Date: Sep. 12, 2019

(65) Prior Publication Data
US 2021/0034969 A1 Feb. 4, 2021

Related U.S. Application Data

(60) Provisional application No. 62/640,946, filed on Mar. 9, 2018.

(51) Int. Cl.
*G06N 3/08* (2023.01)
*G06N 3/045* (2023.01)

(52) U.S. Cl.
CPC .............. *G06N 3/08* (2013.01); *G06N 3/045* (2023.01)

(58) Field of Classification Search
None
See application file for complete search history.

(56) References Cited

U.S. PATENT DOCUMENTS

| 5,043,885 A * | 8/1991 | Robinson .............. G06F 12/124 |
| | | 711/136 |
| 10,254,759 B1 * | 4/2019 | Faust ..................... G06N 3/006 |

(Continued)

FOREIGN PATENT DOCUMENTS

WO WO-2017031356 A1 * 2/2017 ............. G06N 10/00

OTHER PUBLICATIONS

Graves et al., "Hybrid computing using a neural network with dynamic external memory," Nature, Oct. 2016, 538(7626):471-516 (Year: 2016).*

(Continued)

*Primary Examiner* — Abdullah Al Kawsar
*Assistant Examiner* — Asher H. Jablon
(74) *Attorney, Agent, or Firm* — Fish & Richardson P.C.

(57) ABSTRACT

Methods, systems, and apparatus, including computer programs encoded on a computer storage medium, for training a memory-based prediction system configured to receive an input observation characterizing a state of an environment interacted with by an agent and to process the input observation and data read from a memory to update data stored in the memory and to generate a latent representation of the state of the environment. The method comprises: for each of a plurality of time steps: processing an observation for the time step and data read from the memory to: (i) update the data stored in the memory, and (ii) generate a latent representation of the current state of the environment as of the (Continued)

time step; and generating a predicted return that will be received by the agent as a result of interactions with the environment after the observation for the time step is received.

20 Claims, 6 Drawing Sheets

(56) References Cited

U.S. PATENT DOCUMENTS

| | | | | |
|---|---|---|---|---|
| 11,537,134 | B1* | 12/2022 | Wiest | G06N 3/0455 |
| 2013/0184781 | A1* | 7/2013 | Eskandar | A61N 1/36167 |
| | | | | 607/45 |
| 2017/0140266 | A1* | 5/2017 | Wang | G06N 3/092 |
| 2017/0372696 | A1* | 12/2017 | Lee | G10L 15/02 |
| 2019/0095130 | A1* | 3/2019 | Xu | G06N 3/063 |
| 2019/0188463 | A1* | 6/2019 | Sodhani | G06V 10/82 |
| 2019/0244099 | A1* | 8/2019 | Schaul | G06N 3/08 |
| 2019/0251437 | A1* | 8/2019 | Finn | G06N 3/045 |

OTHER PUBLICATIONS

Watabe-Uchida et al., "Neural Circuitry of Reward Prediction Error," 2017, Annu. Rev. Neurosci. 2017. 40:373-94 (Year: 2017).*
Gulcehre et al. Memory Augmented Neural Networks with Wormhole Connections. arXiv preprint arXiv:1701.08718v1 [cs.LG]. 2017 (Year: 2017).*
Office Action in European Appln. No. 19710392.2, dated Nov. 3, 2022, 7 pages.
Bahdanan et al., "Neural Machine Translation by Jointly Learning to Align and Translate," CoRR, Sep. 2014, https://arxiv.org/abs/1409.0473, 15 pages.
Bastos et al., "Canonical Microcircuits for Predictive Coding," Neuron, Nov. 2012, 76(4):695-711.
Beattie et al., "DeepMind Lab," CoRR, Dec. 2016, https://arxiv.org/abs/1612.03801, 11 pages.
Brady et al., "Visual long-term memory has a massive storage capacity for object details," Proceedings of the National Academy of Sciences, Sep. 2008, 105(38):14325-14329.
Chung et al., "A Recurrent Latent Variable Model for Sequential Data," Advances in Neural Information Processing Systems, 2015, 9 pages.
Clayton et al., "Episodic-like memory during cache recovery by scrub jays," Nature, Sep. 1998, 395:272-274.
Corbit et al., "The Role of the Hippocampus in Instrumental Conditioning," Journal of Neuroscience, Jun. 2000, 20(11):4233-4239.
Dayan et al., "Improving Generalization for Temporal Difference Learning: The Successor Representation," Neural Computation, Jul. 1993, 5(4):613-624.
Duan et al., "One-Shot Imitation Learning," CoRR, Dec. 2017, https://arxiv.org/abs/1703.07326, 27 pages.
Dumoulin et al., "A guide to convolution arithmetic for deep learning," CoRR, Jan. 2016, https://arxiv.org/abs/1603.07285, 31 pages.
Eliasmith et al., "A Large-Scale Model of the Functioning Brain," Science, Nov. 2012, 338(6111):1202-1205.
Finkelstein et al., "3-D Maps and Compasses in the Brain," Annual Review of Neuroscience, Jul. 2016, 39(39):171-196.
Gemici et al., "Generative Temporal Models with Memory," CoRR, Feb. 2017, https://arxiv.org/abs/1702.04649, 25 pages.
Gluck et al., "Hippocampal mediation of stimulus representation: A computational theory," Hippocampus, Oct. 1993, 3(44):491-516.
Graves et al., "Hybrid computing using a neural network with dynamic external memory," Nature, Oct. 2016, 538(7626):471-476.
Graves et al., "Speech recognition with deep recurrent neural networks," 2013 IEEE International Conference on Acoustics, Speech and Signal Processing, May 26-31, 2013, pp. 6645-6649.
He et al., "Deep Residual Learning for Image Recognition," Proceedings of the IEEE Conference on Computer Vision and Pattern Recognition, 2016, pp. 770-778.
Hermann et al., "Grounded Language Learning in a Simulated 3D World," CoRR, Jun. 2017, https://arxiv.org/abs/1706.06551, 22 pages.
Higgins et al., "DARLA: Improving Zero-Shot Transfer in Reinforcement Learning," CoRR, Jul. 2017, https://arxiv.org/abs/1707.08475, 15 pages.
Hindy et al., "Linking pattern completion in the hippocampus to predictive coding in visual cortex," Nature Neuroscience, Apr. 2016, 19(5):665-667.
Hochreiter et al., "Long Short-Term Memory," Neural Computation, Nov. 1997, 9(8):1735-1780.
Howard et al., "A distributed representation of temporal context," Journal of Mathematical Psychology, 2002, 46(3):269-299.
Hunt et al., "A distributed, hierarchical and recurrent framework for reward-based choice," Nature Reviews Neuroscience, 2017, 18:172-182.
Jaderberg et al., "Reinforcement Learning with Unsupervised Auxiliary Tasks," CoRR, Nov. 2016, https://arxiv.org/abs/1611.05397, 14 pages.
Kalman et al., "A New Approach to Linear Filtering and Prediction Problems," Journal of Basic Engineering, Mar. 1960, 82(1):35-45.
Kingma et al., "Adam: A Method for Stochastic Optimization," CoRR, Dec. 2014, https://arxiv.org/abs/1412.6980, 15 pages.
Kingma et al., "Auto-Encoding Variational Bayes," CoRR, Dec. 2013, https://arxiv.org/abs/1312.6114, 14 pages.
Kok et al., "Less Is More: Expectation Sharpens Representations in the Primary Visual Cortex," Neuron, Jul. 2012, 75(2):265-270.
Lake et al., "Human-level concept learning through probabilistic program induction," Science, Dec. 2015, 350(6266):1332-1338.
LeCun et al., "Handwritten digit recognition with a backpropagation network," Advances in Neural Information Processing Systems, 1990, pp. 396-404.
Ioffe et al., "Batch Normalization: Accelerating Deep Network Training by Reducing Internal Covariate Shift," CoRR, Feb. 2015, https://arxiv.org/abs/1502.03167, 11 pages.
Luck et al., "The capacity of visual working memory for features and conjunctions," Nature, Nov. 1997, 390:279-281.
Mirowski et al., "Learning to Navigate in Complex Environments," CoRR, Nov. 2016, https://arxiv.org/abs/1611.03673, 16 pages.
Mnih et al., "Asynchronous Methods for Deep Reinforcement Learning," 33rd International Conference on Machine Learning, 2016, pp. 1928-1937.
Mnih et al., "Human-level control through deep reinforcement learning," Nature, Feb. 2015, 518:529-533.
Morris et al., "Developments of a water-maze procedure for studying spatial learning in the rat," Journal of Neuroscience Methods, May 1984, 11(1):47-60.
Moustafa et al., "Why trace and delay conditioning are sometimes (but not always) hippocampal dependent: A computational model," Brain Research, Feb. 2013, 1493:48-67.
Oh et al., "Control of Memory, Active Perception, and Action in Minecraft," CoRR, May 2016, https://arxiv.org/abs/1605.09128, 22 pages.
Oh et al., "Value Prediction Network," CoRR, Nov. 2017, https://arxiv.org/pdf/1707.03497, 16 pages.
PCT International Preliminary Report on Patentability in International Appln. No. PCT/EP2019/055950, dated Sep. 24, 2020, 9 pages.
PCT International Search Report and Written Opinion in International Appln. No. PCT/EP2019/055950, dated Jun. 17, 2019, 16 pages.
Pilley et al., "Border collie comprehends object names as verbal referents," Behavioural Processes, Feb. 2011, 86(2):184-195.
Rao et al., "Predictive coding in the visual cortex: a functional interpretation of some extra-classical receptive-field effects," Nature Neuroscience, Jan. 1999, 2:79.
Rezende et al., "Stochastic backpropagation and variational inference in deep latent gaussian models," International Conference on Machine Learning, 2014, 2: 15 pages.

(56) References Cited

OTHER PUBLICATIONS

Schulman et al., "High-Dimensional Continuous Control Using Generalized Advantage Estimation," CoRR, Jun. 2015, https://arxiv.org/abs/1506.02438, 14 pages.
Seward, "An Experimental Analysis of Latent Learning," Journal of Experimental Psychology, 1949, 39(2):177-186.
Silver et al., "Mastering the game of Go with deep neural networks and tree search," Nature, Jan. 2017, 529:484-489.
Song et al., "Reward-based training of recurrent neural networks for cognitive and value-based tasks," Elife, 2017, 6:e21492.
Stachenfeld et al., "The hippocampus as a predictive map," Nature Neuroscience, Oct. 2017, 20:1643-1653.
Sutton et al., "Policy Gradient Methods for Reinforcement Learning with Function Approximation," Advances in Neural Information Processing Systems, 2000, pp. 1057-1063.
Thistlethwaite, "A critical review of latent learning and related experiments," Psychological Bulletin, 1951, 48(2):97-129.
Todd et al., "Learning to Use Working Memory in Partially Observable Environments through Dopaminergic Reinforcement," Advances in neural information processing systems, 2008, 8 pages.
Tolman, "Cognitive maps in rats and men," Psychological Review, 1948, 55(4):189-208.
Tse et al., "Schemas and Memory Consolidation," Science, Apr. 2007, 316(5821):76-82.
Wang et al., "Learning to reinforcement learn," CoRR, Nov. 2016, https://arxiv.org/abs/1611.05763. 17 pages.
Washburn et al., "A Species Difference in Visuospatial Memory in Adult Humans and Rhesus Monkeys: The Concentration Game," International Journal of Comparative Psychology, 2002, 15(4):288-302.
Wayne [online], "Ext Video 4 for Unsupervised Predictive Memory in a Goal-Directed Agent," Mar. 27, 2018, retrieved on Sep. 17, 2020, <https://www.youtube.com/watch?v=xrYDITXyC6Q&feature=youtu.be>, # pages [Video Submission].
Wayne [online], "Ext. Video 3 for Unsupervised Predictive Memory in a Goal Directed Agent," Mar. 27, 2018, retrieved on Sep. 17, 2020, <https://www.youtube.com/watch?v=dQMKJtLScmk&feature=youtu.be>, # pages [Video Submission].
Wayne [online], "Ext. Video 5 for Unsupervised Predictive Memory in a Goal-Directed Agent," Mar. 27, 2018, retrieved on Sep. 17, 2020, <https://www.youtube.com/watch?v=04H28-qA3f8&feature=youtu.be>, # pages [Video Submission].
Wayne [online], "Ext. Video 6 for Unsupervised Predictive Memory in a Goal-Directed Agent," Mar. 27, 2018, retrieved on Sep. 17, 2020, <https://www.youtube.com/watch?v=3iA19h0Vvq0&feature=youtu.be>, # pages [Video Submission].
Werbos, "Backpropagation through time: what it does and how to do it," Proceedings of the IEEE, Oct. 1990, 78(10):1550-1560.
Weston et al., "Memory Networks," CoRR, Oct. 2014, https://arxiv.org/abs/1410.3916, 15 pages.
Wise et al., "Arbitrary associations between antecedents and actions," Trends in Neurosciences, Jun. 2000, 23(6):271-276.

\* cited by examiner

TRAINING AN UNSUPERVISED MEMORY-BASED PREDICTION SYSTEM TO LEARN COMPRESSED REPRESENTATIONS OF AN ENVIRONMENT

This application is a National Stage Application under 35 U.S.C. § 371 and claims the benefit of International Application No. PCT/EP2019/055950, filed Mar. 11, 2019, which claims priority to U.S. Application No. 62/640,946, filed Mar. 9, 2018, the disclosure of which is incorporated herein by reference.

BACKGROUND

This specification relates to techniques for learning representations of an environment and to reinforcement learning using the representations.

An agent can interact with an environment by performing actions that are selected in response to receiving observations that characterize the current state of the environment. The action to be performed by the agent in response to receiving a given observation can be determined in accordance with the output of a neural network.

Neural networks are machine learning models that employ one or more layers of nonlinear units to predict an output for a received input. Some neural networks are deep neural networks that include one or more hidden layers in addition to an output layer. The output of each hidden layer is used as input to the next layer in the network, i.e., the next hidden layer or the output layer. Each layer of the network generates an output from a received input in accordance with current values of a respective set of parameters.

SUMMARY

This specification describes a system implemented as computer programs on one or more computers in one or more locations that selects actions to be performed by an agent interacting with an environment based on latent representations of the state of the environment generated by a memory-based prediction system.

According to a first aspect there is provided a method for training a memory-based prediction neural network system having a plurality of system parameters, which may be termed memory-based prediction parameters, and configured to receive an input observation characterizing a state of an environment interacted with by an agent and to process the input observation and data read from memory, e.g. an external memory, e.g. memory external to the memory-based prediction neural network system, to update data stored in the external memory and to generate a latent representation of the state of the environment. The method may comprise, for each of a plurality of time steps: receiving an observation for the time step characterizing a current state of the environment being interacted with by the agent at the time step; processing the observation for the time step and data read from the external memory using the memory-based prediction neural network system and in accordance with current values of the memory-based prediction parameters to: (i) update the data stored in the external memory, and (ii) generate a latent representation of the current state of the environment as of the time step; generating, using the latent representation of the current state of the environment as of the time step, a predicted return that will be received by the agent as a result of interactions with the environment after the observation for the time step is received; and determining a gradient based on, for one or more of the time steps, a difference between the predicted return for the time step and an actual return received by the agent; and adjusting the values of the memory-based prediction parameters using the gradient e.g. by backpropagation.

Some advantages of embodiments of the memory-based prediction neural network system are described later. However in broad terms implementations of the training method and trained system enable a paradigm shift for reinforcement learning, which hitherto has employed end-to-end learning, even where external memory is used to store relevant information. By contrast implementations of the above describe method allow a memory-based prediction neural network system to be trained separately from use of the trained system to perform a reinforcement learning (RL) task. That is the system may be trained and then the trained system to learn to perform the RL task and it is not necessary for gradients to be backpropagated from the RL learning into the memory-based prediction neural network system.

In broad terms the system learns a "world model" which may then be used, for example, to produce predictions consistent with a previously observed sensory sequence from the environment. Observations are compressed into low-dimensional state representations, the above-described latent representations, and stored in the memory. This learning is unsupervised, in implementations using a variational autoencoder-like approach. Information from multiple input modalities, i.e. from different components of the observation, may be combined e.g. image and other information, for example egocentric velocity, reward information, action taken information and/or task instruction information. Importantly the predicted return is used to shape the latent representations constructed by unsupervised prediction. This encourages the latent representations to focus on compressing sensory information whilst maintaining information of significance to tasks.

Thus the training method and "world model" constructed by the memory-based prediction neural network system act as a data compression system to capture observations of the environment and to compress and store this information using the latent representations in an efficient manner, in particular focusing on important information as indicated by the actual return received by the agent. In some implementations the observations include image data and reward data, but the method and system may compress other data e.g. data from one or more non-image based sensor streams. Implementations of the above described method used predictive modelling e.g. at least the predicted return but optionally also a predicted reconstruction of the observation, to derive the compressed, latent representations of the environment.

The stored data may be retrieved and used, for example in an RL task or in any other way, for example to reconstruct a version of part of all of the observations. In implementations, though not essentially, learning of the RL task may be performed separately to learning the "world model", e.g. after performing the above described training method. In the context of an RL system learning using the "world model" enables the RL system to learn rapidly and to learn to perform e.g. visuomotor tasks which other systems cannot. In implementations the stored data comprises the latent representations; for example when a latent representation has been derived it may be stored in the external memory to thereby update the external memory In implementations the observation, which may comprise information from multiple input modalities, is encoded using an encoder. Thus processing the observation may comprise processing, using an encoding system and in accordance with current values of encoding system parameters, an input comprising the observation for the time step to generate an encoded representation of the observation. The encoding system may comprise a neural network; it may comprise multiple sub-networks one to encode each observation component, e.g. image, reward, and so forth.

The memory-based prediction neural network system may also include a representation system, in implementations comprising a prior neural network and a posterior neural network. The representation system processes the encoded observation and data read from the memory (at a previous time step) to generate the latent representation i.e. state representation for the current time step. Thus processing the observation may also comprise processing, using a representation system and in accordance with current values of representation system parameters, an input comprising the encoded representation and data read from the external memory at a previous time step to generate the latent representation of the current state of the environment as of the time step.

Processing the observation may also comprise reading data from the memory, for example for use in the next time step. In broad terms data may be read from the memory using a content-based approach based on a similarity between a read key and the stored data e.g. a latent representation. The read may be a soft read, that is based on a weighted sum of the stored data (latent representations); one or more read heads may be employed. A read key may be derived from a history of previous latent (state) representations and previous actions, e.g. from an output of a recurrent neural network having the latent representation and selected action, and optionally the data read from memory, as an input at each time step.

Thus reading data from the external memory using the latent representation may comprises processing, using a recurrent neural network and in accordance with current values of recurrent neural network parameters, an input comprising: (i) the latent representation, (ii) the data read from the external memory at the previous time step, and (iii) an action performed by the agent at the time step, to generate a recurrent neural network output. Data may then be read from the external memory-based on the recurrent neural network output e.g. by providing the recurrent neural network with one or more read heads each to provide a read key used to find matching items in the memory.

Processing the observation may also comprise writing data to the external memory using the latent representation. For example the latent representation of the current observation may be written to the memory e.g. to a storage location in the memory (rather than, say, a soft write), e.g. to a row of a memory matrix.

Thus writing data to the external memory using the latent representation may comprise writing the latent representation to a location, i.e. to a specific or single location in the external memory.

The utility of the memory can be further increased by storing a latent (state) representation together with a representation of the events which occurred after it in time. This may be termed retroactive memory updating. For example for navigation this allows perceptual information relating to a way point to be stored together with information about a subsequently experienced goal. This may be implemented by storing, together with a latent (state) representation for a current time, a weighted sum of latent representations produced after the current time, e.g. by storing them concatenated in the same row of the memory matrix. Thus writing data to the external memory may also comprise updating data previously written to the external memory using the latent representation.

In implementations a decoding system e.g. a one or more decoder neural networks is provided to generate, from the latent (state) representation, the predicted return and optionally to provide reconstructed input data i.e. a (predicted) reconstruction of one or more components of the input observation. This enables the system parameters i.e. the memory-based prediction parameters and in particular the representation system parameters, to be trained using a reconstruction loss. Thus generating the predicted return may comprise processing, using a decoding system and in accordance with current values of decoding system parameters, a decoding system input to generate the predicted return, wherein the decoding system input comprises: (i) the latent representation, and (ii) an action selection policy output used by the agent to select an action to be performed at the time step, an action performed by the agent at the time step, or both. Where the decoding system also generates a predicted reconstruction of the observation for a time step the training method may further comprise determining an additional gradient based on, for one or more of the time steps, a difference between: (i) the predicted reconstruction of the observation for the time step, and (ii) the observation for the time step. The method may then adjust the values of the memory-based prediction parameters, in particular values of the representation system parameters, using the additional gradient.

In some implementations the representation system comprises a prior neural network and a posterior neural network. The prior neural network may generate parameters of a prior probability distribution for the current latent (state) representation, e.g. mean and (log) standard deviation for a (multivariate) Gaussian distribution. This probability distribution may be conditioned on the history of previous latent (state) representations and previous actions, e.g. on the output of the previously described recurrent neural network. The posterior neural network may generate parameters of a posterior probability distribution for the current latent (state) representation, e.g. mean and (log) standard deviation for another (multivariate) Gaussian distribution, conditioned on the same history and also on the encoded representation of the current observation, as well as optionally on the data read from memory. Incorporating the observation allows the posterior probability distribution to better estimate the current latent (state) representation. The current latent (state) representation may be generated by sampling from the posterior probability distribution; this may then be stored in the memory and optionally provided to an RL system, e.g. to an action selection (policy) neural network of the RL system. This approach allows the values of the memory-based prediction parameters, including values of the encoding system and decoding system parameters, to be adjusted i.e. trained using a divergence loss between the prior and posterior probability distributions.

Thus in some implementations the method includes processing, using the prior neural network and in accordance with current values of prior neural network parameters, an input comprising: (i) the recurrent neural network output, and (ii) the data read from the external memory at the previous time step, to generate parameters of a prior probability distribution over a latent representation space. Similarly the method may further include processing, using the posterior neural network and in accordance with current values of posterior neural network parameters, and input comprising: (i) the parameters of the prior probability distribution, (ii) the encoded representation of the observation, (iii) the recurrent neural network output, and (iv) the data read from the external memory at the previous time step, to generate parameters of a posterior probability distribution over the latent representation space. The method may then also include generating the latent representation by sampling a latent representation from the posterior probability distribution.

In some implementations the parameters of the prior probability distribution include prior mean parameters and prior standard deviation parameters, and the parameters of the posterior probability distribution include posterior mean parameters and posterior standard deviation parameters. Sampling a latent representation from the posterior probability distribution may then include sampling from a Normal i.e. Gaussian distribution defined by these parameters. Use of a Normal distribution is convenient but not essential.

The training method may include determining an additional, "divergence" gradient based on, for one or more of the time steps, a measure of similarity between: (i) the prior probability distribution over the latent representation space at the time step, and (ii) the posterior probability distribution over the latent representation space at the time step. Thus an objective function for the training method may include this measure of similarity and the divergence gradient may be a gradient of this measure of similarity. The method may then include adjusting the values of the memory-based prediction parameters using this divergence gradient e.g. by backpropagating the gradient.

The decoder may comprise a return prediction decoder with a state-value function neural network an advantage function neural network. The return prediction may comprise the sum of the outputs from these neural networks.

Thus in some implementations the method may generate a predicted return by processing, using a state-value function neural network and in accordance with current values of state-value function neural network parameters, an input comprising: (i) the latent representation, and (ii) the action selection policy output used by the agent to select the action to be performed at the time step, to generate a state-value estimate. In implementations the method may further comprise processing, using an advantage function neural network and in accordance with current values of advantage function neural network parameters, an input comprising: (i) the latent representation for the time step, and (ii) the action performed by the agent at the time step, to generate an advantage estimate. The method may then generate the predicted return based on the state-value estimate and the advantage estimate. The action selection policy output used by the agent to select an action to be performed at the time step may comprise a score distribution over a predetermined set of possible actions that could be performed by the agent.

Once trained, the memory-based prediction neural network system may be used, for example, for selecting an action to be performed by an agent interacting with an environment. Thus the method may further comprise receiving a latent representation of a current state of the environment, wherein the latent representation of the current state of the environment is generated by a memory-based prediction neural network system that is trained as described above. The method may then further comprise processing, using an action selection neural network system and in accordance with current values of action selection system parameters, an input comprising the latent representation of the current state of the environment to generate an action selection policy output. The method may then select the action to be performed by the agent based on the action selection policy output. This may include reading data from an external memory, updated as described above, and providing this to the action selection neural network system. In some implementations the RL system includes a recurrent neural network for processing, in accordance with current values of recurrent neural network parameters, the action selection neural network system input to generate a recurrent neural network output. The action selection neural network may then process an input comprising: (i) the recurrent neural network output, and (ii) the latent representation, to generate an action selection policy output. Such methods may include determining gradients based on the action selection policy output and adjusting values of the action selection system parameters, but in implementations not values of the memory-based prediction parameters, using the gradients. In some implementations the action selection policy output comprises a score distribution over a predetermined set of possible actions that could be performed by the agent and selecting the action to be performed by the agent based on the action selection policy output comprises sampling an action from the predetermined set of possible actions based on the score distribution.

In some implementations the agent is a mechanical agent, such as a robot or vehicle; this may be operating in a real-world environment. The observation may then includes one or more images e.g. video images. The actions may then comprise actions to be taken by the mechanical agent to perform a mechanical task such as locomotion, navigation, assembly of a component and the like.

Particular embodiments of the subject matter described in this specification can be implemented so as to realize one or more of the following advantages.

Some conventional memory systems that operate in conjunction with an action selection system must be trained jointly with the action selection system using a reinforcement learning objective function. Conventional memory systems and action selection systems trained in this manner may perform poorly in solving tasks that involve long delays between relevant stimuli (e.g., represented in observations of the environment) and later decisions (e.g., actions performed by the agent). Examples of such tasks include tasks involving navigation back to previously visited goals and tasks involving rapid reward valuation (i.e., where the agent must understand the value of different objects after a few exposures). For example, a conventional memory system that is jointly trained with an action selection system may perform poorly if the number of time steps over which the gradient of the reinforcement learning objective is calculated is smaller than the number of time steps over which information needs to be stored and retrieved. The number of time steps over which the gradient is calculated defines the duration of time over which the system can assign credit or blame to system dynamics or information storage events leading to success or failure. Increasing the number of time steps over which the gradient is calculated may be infeasible because it may result in unacceptably high levels of computational complexity and latency during training.

The memory-based prediction (MBP) system described in this specification operates in conjunction with an action selection system by generating latent representations of states of an environment being interacted with by an agent and providing the latent representations for use in selecting actions to be performed by the agent. The MBP system can be trained by a predictive modeling process to generate latent representations that are predictive of: (i) subsequent latent representations of subsequent states of the environment, (ii) the return that will be received by the agent as a result of interactions with the environment, or both. The MBP system and the action selection system can be trained end-to-end using a reinforcement learning objective function, but do not have to be. That is, the MBP system can be trained using the "unsupervised" predictive modeling process independently of the "supervised" reinforcement learning objective.

Training the MBP system using the predictive modeling process, rather than relying entirely on end-to-end training using the reinforcement learning objective, enables an action selection system operating in conjunction with the MBP system to "solve" tasks that involve long time delays between relevant stimuli and later decisions. Action selection systems operating in conjunction with conventional memory systems may be unable to solve such tasks. In cases where action selection systems operating in conjunction with conventional memory systems can solve such tasks, training them may consume substantially more computational resources (e.g., memory and computing power) than training the MBP system described in this specification.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes a memory-based prediction (MBP) system and an action selection system.

The MBP system is configured to compress observations characterizing the state of an environment being interacted with by an agent to generate lower-dimensional "latent" representations of the state of the environment by a predictive modeling process. In particular, the MBP system can generate a latent representation of a state of the environment that encodes information that is both: (i) relevant to a task being performed by the agent, and (ii) predictive of latent representations of subsequent states of the environment. The MBP system stores the latent representations of the states of the environment in a memory.

The action selection system selects actions to be performed by the agent at each of multiple time steps. The action selection system selects the action to be performed at each time step by processing: (i) the latent representation of the current state of the environment generated by the MBP system, and (ii) data read from the memory maintained by the MBP system.

Figure 1:
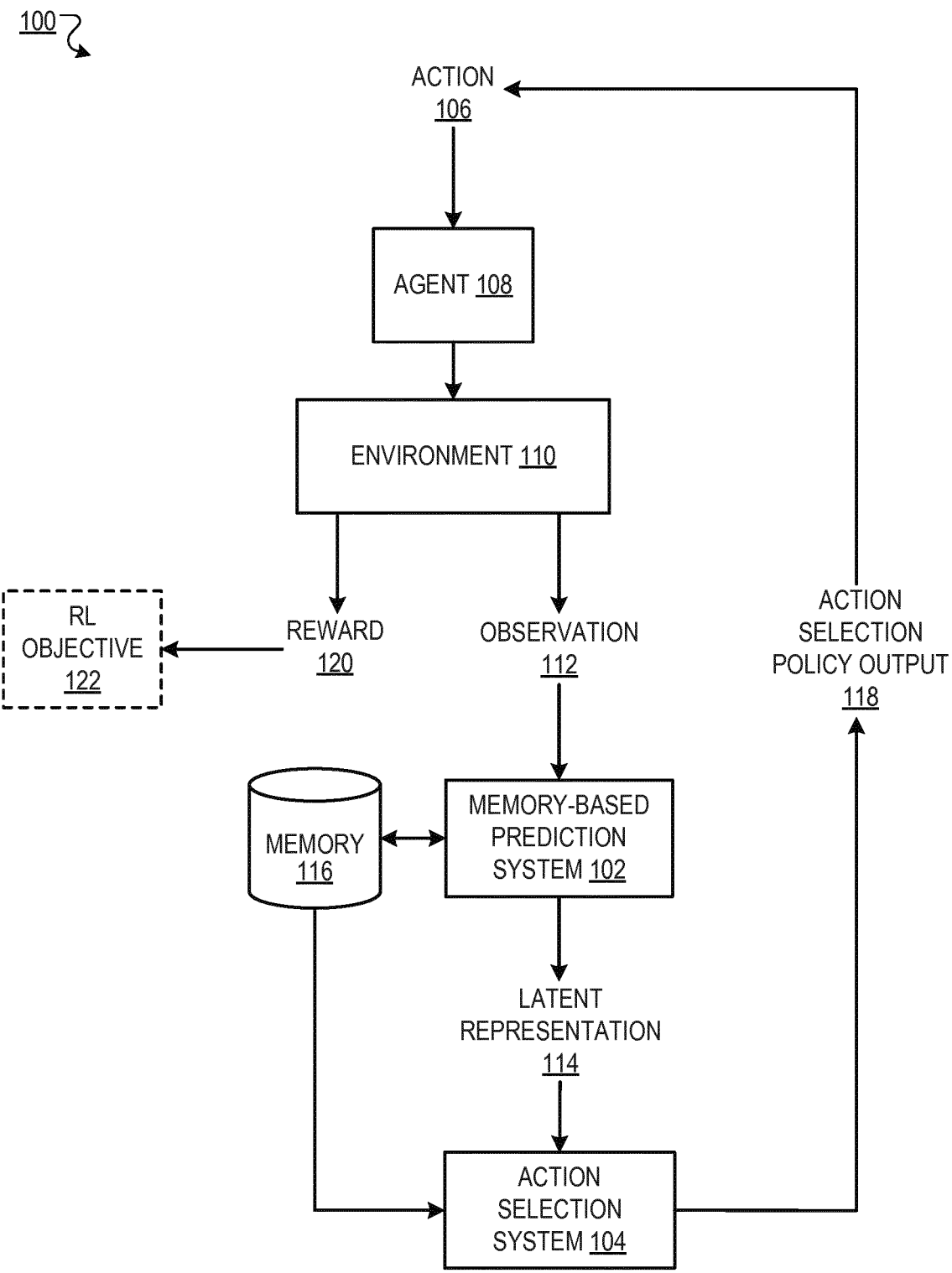
FIG. 1 illustrates an example data flow for using a memory-based prediction system and an action selection system to select actions to be performed by an agent interacting with an environment at each of multiple time steps.

FIG. 1 illustrates an example data flow 100 for using an MBP system 102 and an action selection system 104 to select actions 106 to be performed by an agent 108 interacting with an environment 110 at each of multiple time steps.

At each time step, the MBP system 102 processes data characterizing the current state of the environment 110, referred to as an observation 112, to generate a latent representation 114 of the current state of the environment 110. The latent representation 114 of the current state of the environment 110 is represented as an ordered collection of numerical values, for example, a vector of numerical values, and generally has a lower dimensionality than the observation 112.

The MBP system 102 stores the latent representation 114 generated at each time step in a memory 116 (e.g., a logical data storage area or physical data storage device). The contents of the memory 116 can be represented as a two-dimensional matrix, where each row of the matrix stores a latent representation of the state the environment at a respective time step, and optionally, a discounted sum of latent representations generated at time steps subsequent to the respective time step. For example, each row of the matrix may store: $[z_t, (1-\gamma)\Sigma_{t'>t}\gamma^{t'-t}z_{t'}]$, where $z_t$ is the latent representation at time step t, $z_{t'}$ is the latent representation at time step t' subsequent to time step t, and $\gamma$ is a discount factor between 0 and 1.

The action selection system 104 processes the latent representation 114 of the current state of the environment 110 and data "read" (i.e., obtained) from the memory 116 to generate an action selection policy output 118. The policy output 118 is used to select an action 106 to be performed by the agent 108 at the current time step. For example, the policy output 118 generated by the action selection system 104 at each time step may include a respective numerical probability value for each action in a set of possible actions that can be performed by the agent at the time step. In some implementations, the action 106 to be performed by the agent 108 at the current time step can be determined by sampling an action in accordance with the probability values for the actions. In some other implementations, the action with the highest probability value may be selected as the action to be performed by the agent 108 at the current time step. As another example, the policy output 118 may directly define the action to be performed by the agent, for example, by indexing an action in a set of possible actions that can be performed by the agent. As another example, the policy output 118 may include a respective Q-value for each action in a set of possible actions that can be performed by the agent. In this example, the Q-values can be processed (e.g., using a soft-max function) to generate a respective probability value for each possible action, which can be processed (as described earlier) to select the action to be performed by the agent.

At each time step, the state of the environment 110 at the time step (as characterized by the observation 112) depends on the state of the environment 110 at the previous time step and the action 106 performed by the agent 108 at the previous time step. Moreover, the agent 108 may receive a reward 120 based on the current state of the environment 110 and the action 106 of the agent 108 at the time step. In general, the reward 120 is a numerical value. The reward 120 can be based on any event or aspect of the environment. For example, the reward 120 may indicate whether the agent 108 has accomplished a task (e.g., navigating to a target location in the environment 110) or the progress of the agent 108 towards accomplishing a task.

In some implementations, the environment is a real-world environment and the agent is a mechanical agent interacting with the real-world environment. For example, the agent may be a robot interacting with the environment to accomplish a specific task, e.g., to locate an object of interest in the environment or to move an object of interest to a specified location in the environment or to navigate to a specified destination in the environment; or the agent may be an autonomous or semi-autonomous land or air or sea vehicle navigating through the environment.

In these implementations, the observations may include, for example, one or more of images, object position data, and sensor data to capture observations as the agent as it interacts with the environment, for example sensor data from an image, distance, or position sensor or from an actuator.

For example in the case of a robot the observations may include data characterizing the current state of the robot, e.g., one or more of: joint position, joint velocity, joint force, torque or acceleration, for example gravity-compensated torque feedback, and global or relative pose of an item held by the robot.

In the case of a robot or other mechanical agent or vehicle the observations may similarly include one or more of the position, linear or angular velocity, force, torque or acceleration, and global or relative pose of one or more parts of the agent. The observations may be defined in 1, 2 or 3 dimensions, and may be absolute and/or relative observations.

The observations may also include, for example, sensed electronic signals such as motor current or a temperature signal; and/or image or video data for example from a camera or a LIDAR sensor, e.g., data from sensors of the agent or data from sensors that are located separately from the agent in the environment.

In the case of an electronic agent the observations may include data from one or more sensors monitoring part of a plant or service facility such as current, voltage, power, temperature and other sensors and/or electronic signals representing the functioning of electronic and/or mechanical items of equipment.

In these implementations, the actions may be control inputs to control the robot, e.g., torques for the joints of the robot or higher-level control commands, or the autonomous or semi-autonomous land or air or sea vehicle, e.g., torques to the control surface or other control elements of the vehicle or higher-level control commands.

In other words, the actions can include for example, position, velocity, or force/torque/acceleration data for one or more joints of a robot or parts of another mechanical agent. Action data may additionally or alternatively include electronic control data such as motor control data, or more generally data for controlling one or more electronic devices within the environment the control of which has an effect on the observed state of the environment. For example in the case of an autonomous or semi-autonomous land or air or sea vehicle the actions may include actions to control navigation e.g. steering, and movement e.g., braking and/or acceleration of the vehicle.

In some implementations the environment is a simulated environment and the agent is implemented as one or more computers interacting with the simulated environment.

For example the simulated environment may be a simulation of a robot or vehicle and the reinforcement learning system may be trained on the simulation. For example, the simulated environment may be a motion simulation environment, e.g., a driving simulation or a flight simulation, and the agent is a simulated vehicle navigating through the motion simulation. In these implementations, the actions may be control inputs to control the simulated user or simulated vehicle.

In another example, the simulated environment may be a video game and the agent may be a simulated user playing the video game.

In a further example the environment may be a protein folding environment such that each state is a respective state of a protein chain and the agent is a computer system for determining how to fold the protein chain. In this example, the actions are possible folding actions for folding the protein chain and the result to be achieved may include, e.g., folding the protein so that the protein is stable and so that it achieves a particular biological function. As another example, the agent may be a mechanical agent that performs or controls the protein folding actions selected by the system automatically without human interaction. The observations may include direct or indirect observations of a state of the protein and/or may be derived from simulation.

In a similar way the environment may be a drug design environment such that each state is a respective state of a potential pharma chemical drug and the agent is a computer system for determining elements of the pharma chemical drug and/or a synthetic pathway for the pharma chemical drug. The drug/synthesis may be designed based on a reward derived from a target for the drug, for example in simulation. As another example, the agent may be a mechanical agent that performs or controls synthesis of the drug.

Generally in the case of a simulated environment the observations may include simulated versions of one or more of the previously described observations or types of observations and the actions may include simulated versions of one or more of the previously described actions or types of actions.

In some other applications the agent may control actions in a real-world environment including items of equipment, for example in a data center or grid mains power or water distribution system, or in a manufacturing plant or service facility. The observations may then relate to operation of the plant or facility. For example the observations may include observations of power or water usage by equipment, or observations of power generation or distribution control, or observations of usage of a resource or of waste production. The agent may control actions in the environment to increase efficiency, for example by reducing resource usage, and/or reduce the environmental impact of operations in the environment, for example by reducing waste. The actions may include actions controlling or imposing operating conditions on items of equipment of the plant/facility, and/or actions that result in changes to settings in the operation of the plant/facility e.g. to adjust or turn on/off components of the plant/facility.

In another application, the agent may provide actions to control a renewable power generation system such as a wind or solar farm, e.g. based on predicted wind or solar irradiance, to increase the efficiency of operation of the system.

In some further applications, the environment is a real-world environment and the agent manages distribution of tasks across computing resources e.g. on a mobile device and/or in a data center. In these implementations, the actions may include assigning tasks to particular computing resources.

As further example, the actions may include presenting advertisements, the observations may include advertisement impressions or a click-through count or rate, and the reward may characterize previous selections of items or content taken by one or more users.

In some cases, the observations may include textual or spoken instructions provided to the agent by a third-party (e.g., an operator of the agent). For example, the agent may be an autonomous vehicle, and a user of the autonomous vehicle may provide textual or spoken instructions to the agent (e.g., to navigate to a particular location).

Optionally, in any of the above implementations, the observation at any given time step may include data from a previous time step that may be beneficial in characterizing the environment, e.g., the action performed at the previous time step, the reward received at the previous time step, or both.

The action selection system 104 is trained by using reinforcement learning techniques to iteratively adjust the values of the action selection system parameters to enable the agent 108 to effectively perform tasks. More specifically, the values of the action selection system parameters are adjusted using gradients of a reinforcement learning objective function (i.e., the RL objective 122) with respect to the action selection system parameters to increase a cumulative measure of reward received by the agent by interacting with the environment. The action selection system 104 can be trained using any appropriate reinforcement learning technique, for example, a Q-learning technique or a policy gradient technique.

Optionally, reinforcement learning techniques can be used to train the MBP system 102 by iteratively adjusting the values of the MBP system parameters using gradients of the RL objective 122 with respect to the MBP system parameters. That is, the MBP system 102 and the action selection system 104 can be trained "end-to-end" using gradients of the RL objective 122. However, the MBP system 102 can also be trained independently of the RL objective 122 (that is, the MBP system 102 and the action selection system 104 need not be trained end-to-end). In particular, as will be described in more detail below, the MBP system 102 can be trained using gradients of a "prediction" objective function and a "divergence" objective function. The prediction objective function encourages the MBP system 102 to generate a latent representation of an observation that can be processed to: (i) reconstruct the observation, and (ii) predict the return received by the agent as a result of interactions with the environment after the observation is received. A "return" is a cumulative measure (e.g., a discounted sum) of rewards received by the agent during interaction with the environment, and can be represented as a numerical value. The divergence objective function encourages the MBP system 102 to generate a latent representation of an observation that is predictive of latent representations of subsequent states of the environment.

The MBP system 102 and the action selection system 104 (i.e., "the systems") may be trained using synchronous or asynchronous distributed machine learning training techniques. More specifically, each of multiple worker computing units (e.g., processors or threads) may use the systems to interact with different instantiations of the environment. Updates to the parameter values of the systems may be determined based on training data generated by each of the worker computing units.

The systems can be located in any appropriate locations. For example, the systems may be located remotely from one another, and communications between them may be transmitted over a data communication network (e.g., the Internet). Alternatively, the systems may be located in the same geographic location (e.g., within the same data center).

Figure 2:
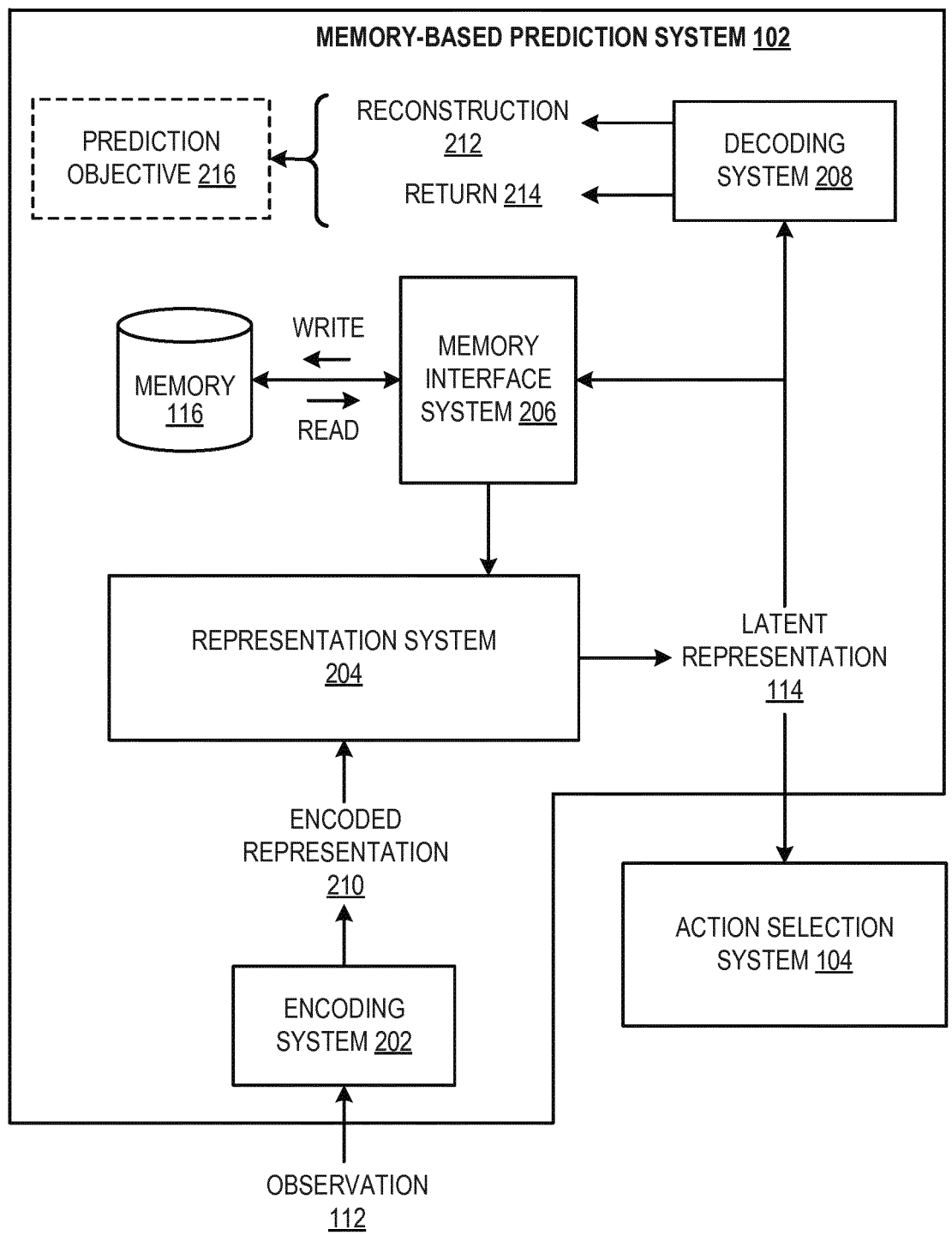
FIG. 2 is a block diagram of an example memory-based prediction system.

FIG. 2 is a block diagram of an example MBP system 102. The MBP system 102 is an example of a system implemented as computer programs on one or more computers in one or more locations in which the systems, components, and techniques described below are implemented.

At each of multiple time steps, the MBP system 102 is configured to process an observation 112 characterizing a current state of the environment at the time step to generate a latent representation 114 of the observation 112. The MBP system 102 stores the latent representation 114 in the memory 116 and provides it to the action selection system 104 for use in selecting an action to be performed by the agent at the time step.

As described earlier, the observation 112 can include multiple "components", including one or more of: data captured by one or more sensors of the agent (e.g., an image of the environment captured by a camera sensor of the agent), a velocity of the agent, a textual or spoken instruction provided to the agent, the reward received by the agent at the previous time step, and the action performed by the agent at the previous time step. Each component of the observation 112 can be represented as an ordered collection of numerical values, for example, a vector or matrix of numerical values. For example, an image of the environment can be represented by one or more channels, where each channel is a two-dimensional (2D) matrix of numerical values that corresponds to a respective color (e.g., red, green, or blue). As another example, the action performed by the agent at the previous time step can be represented as a "one-hot" vector of numerical values.

The MBP system 102 includes an encoding system 202, a representation system 204, a memory interface system 206, the memory 116, and a decoding system 208.

At each time step, the encoding system 202 is configured to process the current observation 112 to generate an encoded representation 210 of the observation 112 as an ordered collection of numerical values (e.g., a vector or matrix of numerical values). To generate the encoded representation 210 of the observation 112, the encoding system 202 may process one or more components of the observation 112 using respective encoding neural networks. For example, the encoding system 202 can process an image of the environment included in the observation 112 using a convolutional image encoding neural network to generate an encoded representation of the image. As another example, the encoding system 202 may sequentially process the characters of a textual instruction included in the observation 112 using a long short-term memory (LSTM) recurrent text encoding neural network to generate an encoded representation of the textual instruction. The encoding system 202 may generate the overall encoded representation 210 by concatenating respective encoded representations of each component of the observation 112 into a vector. The encoding system 202 may concatenate certain components of the observation 112 directly onto the encoded representation 210 without further processing, for example, the reward received by the agent at the previous time step (which is represented as a single numerical value).

The representation system 204 is configured to process: (i) the encoded representation 210 of the observation 112, and (ii) data read from the memory 116 at the previous time step by the memory interface system 206, to generate the latent representation 114 of the observation 112. The latent representation 114 is represented as an ordered collection of numerical values, for example, a vector of numerical values. The representation system 204 is described in more detail with reference to FIG. 3.

The memory interface system 206 is configured to read data from the memory 116, and afterwards, to write data to the memory 116.

To read data from the memory 116, the memory interface system 206 processes the latent representation 114 using a recurrent neural network to generate a recurrent neural network output. Optionally, the recurrent neural network may process other inputs in addition to the latent representation 114, for example, data read from the memory 116 by the memory interface system 206 at the previous time step, a representation of the action performed by the agent at the current time step, or both. The memory interface system 206 uses the recurrent neural network output to generate a predetermined number of "read key" vectors. Thereafter, the memory interface system 206 uses each read key vector to obtain a respective "readout" vector from the contents of the memory 116, as will be described in more detail with reference to FIG. 4. The data "read from the memory" refers to the collection of readout vectors obtained from the contents of the memory. The data read from the memory 116 at the current time step is provided to the representation system 204 at the next time step for use in generating the latent representation of the observation at the next time step.

To write data to the memory 116, the memory interface system 206 stores the latent representation 114 in a row of the memory 116. In some implementations, each row of the memory stores: (i) a latent representation for a given time step, and (ii) a discounted sum of latent representations for time steps subsequent to the given time step. In these implementations, in addition to storing the latent representation 114 in a respective row of the memory 116, the memory interface system 206 updates each other row in the memory by updating the discounted sum of subsequent latent representations stored in the row. An example process for writing data to the memory 116 is described in more detail with reference to FIG. 4.

During training of the MBP system 102, the decoding system 208 is configured to process the latent representation 114 to generate: (i) a predicted reconstruction 212 of the observation 112, and (ii) a predicted return 214 that will be received by the agent as a result of interactions with the environment after the observation for the time step is received.

The predicted reconstruction 212 includes a predicted reconstruction of each component of the observation 112. To generate the predicted reconstruction 212 of a given component of the observation 112, the decoding system 208 may process the encoded representation of the given component using a respective decoding neural network. The decoding neural network used to generate the reconstruction of the given component may have the same architecture as the corresponding encoding neural network used to generate the encoded representation of the given component, except the operations are reversed. For example, the decoding system 208 may process the encoded representation of an image included in the observation 112 using a convolutional image decoding neural network, where each convolutional layer of the decoding neural network is a transposition of a corresponding convolutional layer of the convolutional image encoding neural network.

The decoding system 208 generates the predicted return 214 by processing the latent representation 114 and one or both of: (i) the policy output 118 generated by the action selection system 104 at the current time step, and (ii) the action performed by the agent at the current time step. An example process for generating the predicted return 214 is described in more detail with reference to FIG. 4.

The MBP system 102 can jointly train the encoding system 202, the representation system 204, the memory interface system 206, and the decoding system 208 by iteratively adjusting their respective parameter values to enable the MBP system 102 to accurately reconstruct observations and predict returns. More specifically, the MBP system 102 can use a training engine to adjust the values of the MBP system parameters (i.e., including the parameters of the encoding, representation, memory interface, and decoding systems) using gradients of a prediction objective function 216 with respect to the MBP system parameters. The prediction objective 216 may include respective terms that characterize: (i) how accurately the predicted reconstruction 212 approximates the observation 112, and (ii) how accurately the predicted return 214 approximates the actual return received by the agent.

The action selection system 104 is configured to process an input including the latent representation 114 of the current observation 112 and data read from the memory 116 to select the action to be performed by the agent at the current time step. An example process for selecting an action to be performed by the agent at a time step using a latent representation 114 generated by the MBP system 102 is described in more detail with reference to FIG. 5.

Figure 3:
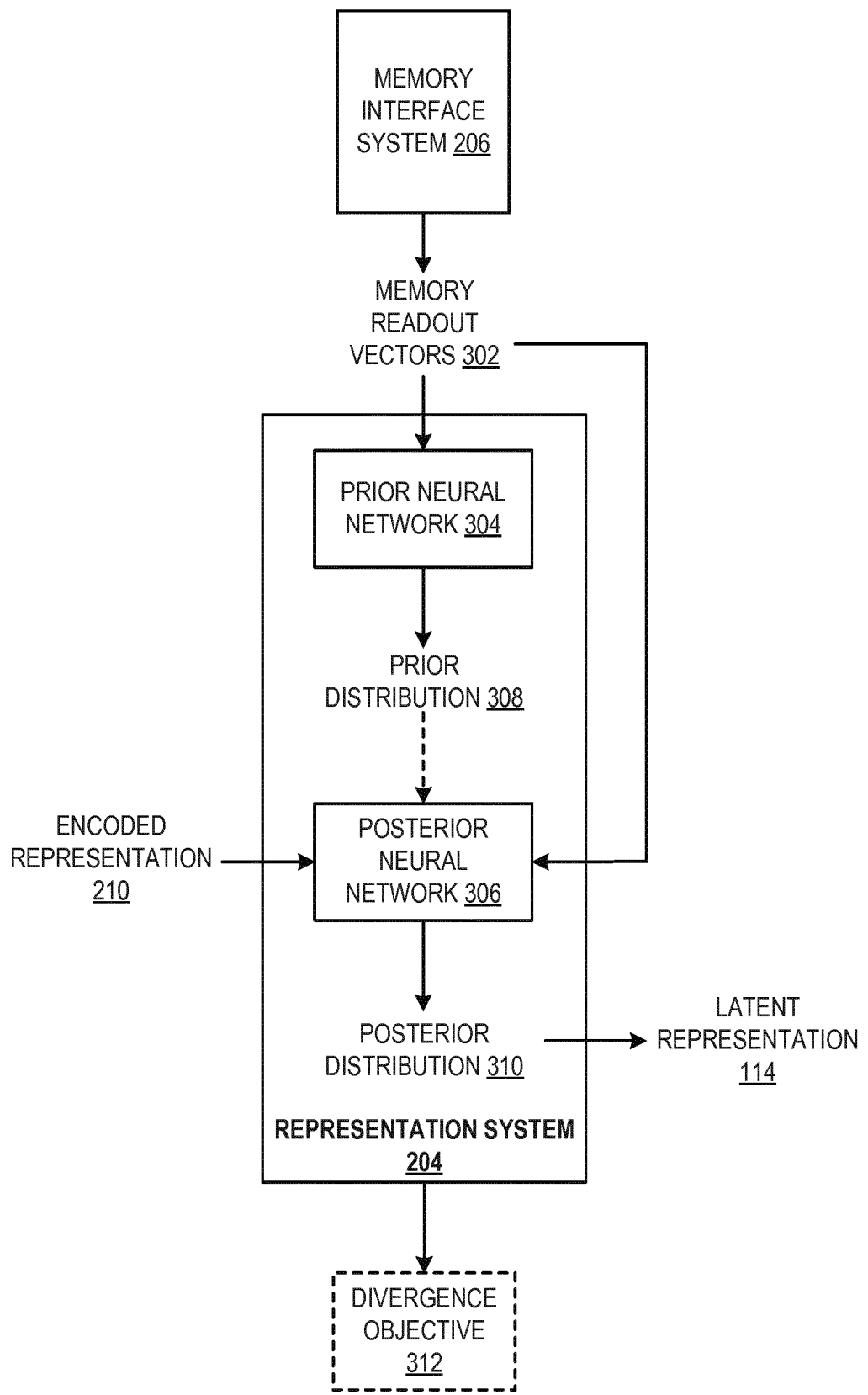
FIG. 3 is a block diagram of an example representation system used by a memory-based prediction system.

FIG. 3 is a block diagram of an example representation system 204. The representation system 204 is an example of a system implemented as computer programs on one or more computers in one or more locations in which the systems, components, and techniques described below are implemented.

The representation system 204 is configured to process: (i) the encoded representation 210 of the current observation, and (ii) data read from the memory at the previous time step (i.e., the memory readout vectors 302), to generate the latent representation 114 of the current observation. The representation system 204 generates the latent representation 114 of the current observation using a prior neural network 304 and a posterior neural network 306.

The prior neural network 304 is configured to process the memory readout vectors 302 to generate data defining the parameters of a prior probability distribution 308 over the "latent representation space" of possible latent representations. For example, for latent representations expressed as n-dimensional vectors, the prior neural network 304 may generate a mean vector and a diagonal covariance matrix of an n-dimensional Normal distribution. Optionally, the prior neural network 304 may process other inputs in addition to the memory readout vectors 302, for example, the output of the recurrent neural network of the memory interface system 206. The prior distribution 308 predicts the latent representation 114 of the current observation 112 based on the memory readout vectors 302 (i.e., which characterize latent representations of previous states of the environment). Generally, the prior neural network 304 generates the prior distribution 308 without processing the encoded representation 210 of the current observation (or other data derived from the current observation).

The posterior neural network 306 is configured to process the encoded representation 210 of the current observation, the memory readout vectors 302, and the parameters of the prior distribution 308, to generate data defining the parameters of a posterior probability distribution 310 over the latent representation space. For example, for latent representations expressed as n-dimensional vectors, the posterior neural network 306 may generate a mean vector and a diagonal covariance matrix of an n-dimensional Normal distribution (similar to the prior neural network 304).

Example architectures of the prior neural network and the posterior neural network are described in more detail with reference to FIG. 4.

The representation system 204 samples the latent representation 114 of the current observation from the posterior distribution 310. As described earlier, the latent representation 114 is thereafter written to the memory 116 and provided to the action selection system 104 for use in selecting an action to be performed by the agent in response to the current observation.

The MBP system 102 uses the training engine to jointly train the MBP system parameters using gradients of a divergence objective function 312 with respect to the MBP system parameters. As will be described in more detail with reference to FIG. 4, the divergence objective 312 includes a similarity measure (e.g., a Kullback-Leibler similarity measure) between the prior distribution 308 and the posterior distribution 310. Training the MBP system parameters using gradients of the divergence objective function 312 enables the representation system 204 to generate a prior distribution 308 based on latent representations of previous states of the environment which is predictive of the latent representation of the current state of the environment. Therefore, training the MBP system parameters using gradients of the divergence objective function 312 enables the representation system to generate latent representations of states of the environment that are predictive of latent representations of subsequent states of the environment. The MBP system parameters refer to the parameters of the prior and posterior neural networks of the representation system 204, as well as the parameters of encoding, memory interface, and decoding systems of the MBP system 102.

Figure 4:
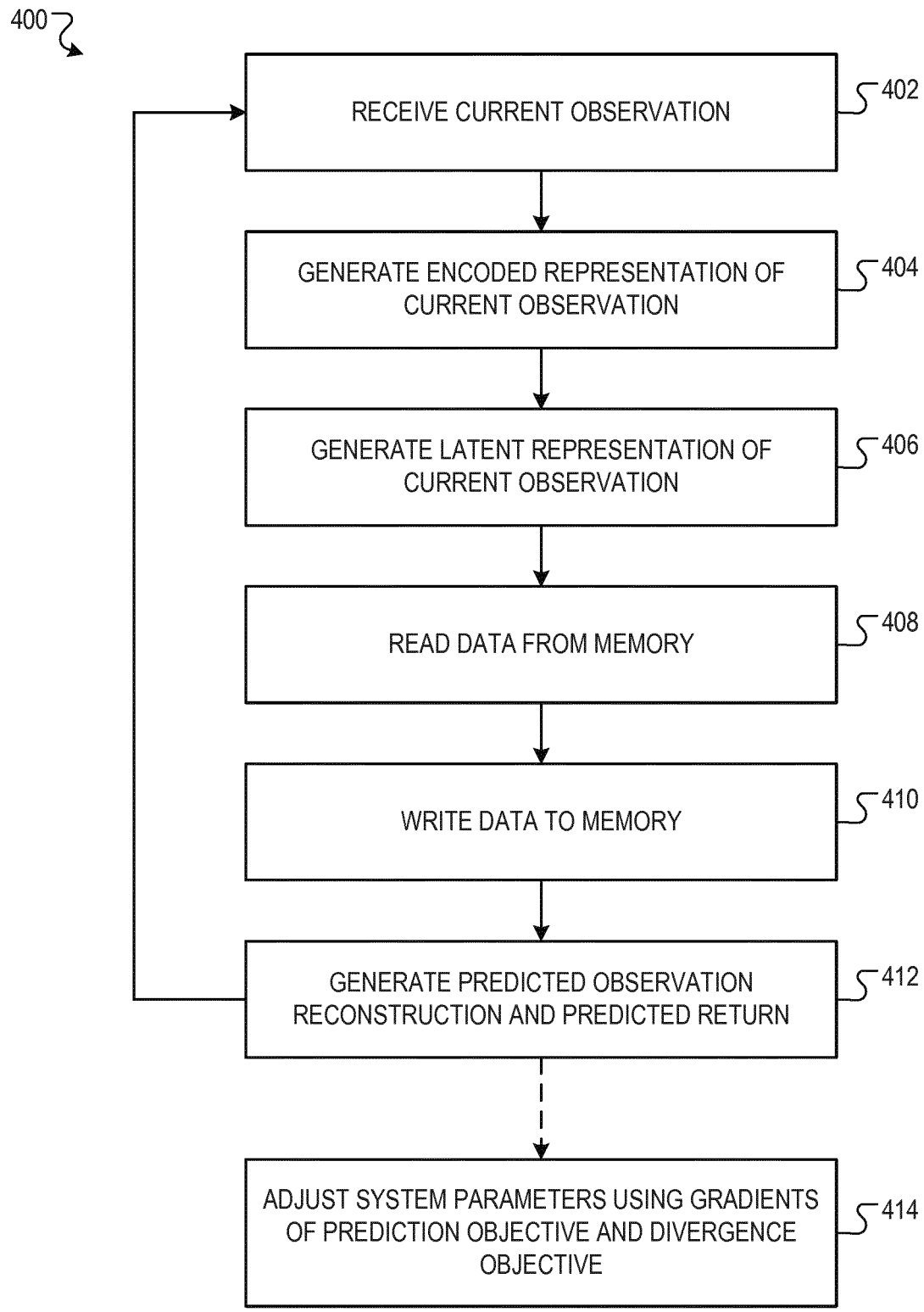
FIG. 4 is a flow diagram of an example process for training a memory-based prediction system.

FIG. 4 is a flow diagram of an example process 400 for training a memory-based prediction system. For convenience, the process 400 will be described as being performed by a system of one or more computers located in one or more locations. For example, a memory-based prediction system, e.g., the memory-based prediction system 102 of FIG. 1, appropriately programmed in accordance with this specification, can perform the process 400.

The system receives a current observation which characterizes a current state of the environment being interacted with by the agent at the current time step (402). The observation can include multiple components, including one or more of: data captured by one or more sensors of the agent, a velocity of the agent, a textual or spoken instruction provided to the agent, the reward received by the agent at the previous time step, and the action performed by the agent at the previous time step.

The system generates an encoded representation of the current observation (404). The system generates the encoded representation of the current observation by processing the current observation using an encoding system, in accordance with current values of encoding system parameters. The encoding system may process one or more components of the current observation using respective encoding neural networks (e.g., a convolutional image encoding neural network and a LSTM recurrent text encoding neural network). After generating a respective encoded representation of each component of the observation, the encoding system may generate the overall encoded representation of the observation by concatenating the respective encoded representations of the components of the observation into a vector.

The system generates a latent representation of the current observation using the encoded representation of the current observation and data read from the external memory at the previous time step (406). The system generates the latent representation of the current observation using a prior neural network and a posterior neural network.

The prior neural network is configured to process the data read from the memory at the previous time step to generate data defining the parameters of a prior probability distribution over the latent representation space of possible latent representations. Optionally, the prior neural network may process other inputs in addition to the data read from the memory, for example, the hidden state of the recurrent neural network of the memory interface system. The prior neural network can have any appropriate neural network architecture. For example, the prior neural network may be a multi-layer perceptron (MLP) with two hidden layers with tanh activation functions and a linear output layer, where each hidden layer and the output layer have width $2 \times |z|$, where $|z|$ is the dimensionality of the latent representations. In one example, the first $|z|$ dimensions of the output of the prior neural network may represent a mean vector of a Normal distribution, and the second $|z|$ dimensions of the output of the prior neural network may represent the components of a diagonal covariance matrix of the Normal distribution.

The posterior neural network is configured to process the encoded representation of the current observation and the data read from the memory at the previous time step to generate data defining the parameters of a posterior probability distribution over the latent representation space. Optionally, the posterior neural network may process other inputs in addition to the encoded representation and the data read from the memory, for example, the parameters of the prior distribution and the output of the recurrent neural network used to read data from the memory at the previous time step. The posterior neural network can have any appropriate neural network architecture. For example, the posterior neural network may be a multi-layer perceptron (MLP) with two hidden layers with tanh activation functions and a linear output layer, where each hidden layer and the output layer have width $2 \times |z|$, where $|z|$ is the dimensionality of the latent representations. In one example, the input layer of the posterior neural network may receive the encoded representation of the current observation, the data read from the memory at the previous time step, and the recurrent neural network output used to read data from the memory at the previous time step. The system may generate the posterior distribution parameters by adding the output of the output layer of the posterior neural network to the prior distribution parameters. The first $|z|$ dimensions of the posterior distribution parameters may represent a mean vector of a Normal distribution, and the second $|z|$ dimensions of the posterior distribution parameters may represent the components of a diagonal covariance matrix of the Normal distribution.

The system reads data from the memory using the latent representation of the current observation (408). To read data from the memory, the system processes an input including the latent representation of the current observation and data read from the memory at the previous time step using a recurrent neural network to generate a recurrent neural network output. Optionally, the input processed by the recurrent neural network may include additional data, for example, a representation of the action performed at the agent by the time step (i.e., which was determined by an action selection system using the latent representation of the current observation).

For example, the recurrent neural network may be an LSTM network with two hidden layers. Denote the input to the LSTM as $x_t$. Within a layer l, there is a recurrent state $h_t^l$ and a "cell" state $s_t^l$, which are updated based on the following recursion (with $\sigma(x)=(1+\exp(-x))^{-1}$):

$$i_t^l = \sigma(W_i^l[x_t, h_{t-1}^l, h_t^{l-1}] + b_i^l) \quad (1)$$

$$f_t^l = \sigma(W_f^l[x_t, h_{t-1}^l, h_t^{l-1}] + b_f^l) \quad (2)$$

$$s_t^l = f_t^l s_{t-1}^l + i_t^l \tanh(W_s^l[x_t, h_{t-1}^l, h_t^{l-1}] + b_s^l) \quad (3)$$

$$o_t^l = \sigma(W_o^l[x_t, h_{t-1}^l, h_t^{l-1}] + b_o^l) \quad (4)$$

$$h_t^l = o_t^l \tanh(s_t^l) \quad (5)$$

where $W_i^l, W_f^l, W_s^l, W_o^l, b_i^l, b_f^l, b_s^l, b_o^l$ represent trainable parameters of the LSTM, and the LSTM recurrent neural network output is given by: $[h_t^1, h_t^2]$.

The system uses the recurrent neural network output to read data from the memory. In particular, the system applies a linear neural network layer to the recurrent neural network output to generate a memory interface vector of dimension $K^r \times (2 \times |z|+1)$, where $K^r$ is a positive integer defining the number of readout vectors to be obtained from memory and $|z|$ is the dimensionality of the latent representation of an observation. The memory interface vector is then segmented into $K^r$ read key vectors $k_t^1, k_t^2, \ldots, k_t^{K^r}$ of length $2 \times |z|$ and $K^r$ scalars $sc_t^1, \ldots, sc_t^{K^r}$, which are passed through the function $\text{SoftPlus}(x) = \log(1+\exp(x))$ to create the scalars $\beta_t^1, \ldots, \beta_t^{K^r}$.

The system computes e.g. the cosine similarity between each read key $k_t^i$ and each memory row $M_{t-1}[j, \cdot]$. The cosine similarity between the i-th ready key and the j-th memory row is denoted by $c_t^{ij}$. For each read key, the system determines a normalized weighting vector of length $N^{mem}$ (where $N^{mem}$ represents the number of rows in the memory) by:

$$w_t^i[j] = \frac{\exp(\beta_t^i c_t^{ij})}{\sum_{j'=1}^{N^{mem}} \exp(\beta_t^i c_t^{ij'})} \quad (6)$$

where $w_t^i[j]$ is the j-th component of the weighting vector for the i-th read key.

For the i-th read key, the system generates a corresponding readout vector $m_t^i$ from memory by summing each row of the memory, where each row of the memory is scaled by the corresponding component of the normalized weighting vector for the i-th read key. That is, the system generates the readout vector $m_t^i = M_{t-1}^T w_t^i$, where $M_{t-1}^T$ represents the transpose of the 2D matrix representing the memory. The data read from the memory is represented as the concatenation of the readout vectors.

At the first time step, the "data read from the memory at the previous time step" should be understood to refer to readout vectors having default values (e.g., all zeros).

The system writes data to the memory using the latent representation of the current observation (410). First, the system identifies a row of the memory where the latent representation of the current observation will be written (i.e., stored). If the memory is not full (i.e., if the system has not previously written data in one or more rows of the memory), the system identifies an unused row of the memory for writing data at the current time step. If the memory is full (i.e., the system has previously written data in each row of the memory), the system identifies a row of the memory for writing data at the current time step based on how frequently data is read from each row of the memory. The system can keep track of how frequently data is read from a row k of the memory by iteratively updating a read counter $u_r[k]$ at each time step t as: $u_r[k] = u_{t-1}[k] + \Sigma_i w_t^i[k]$, where $w_t^i[k]$ is defined with reference to equation 6, and the sum is over the number of read key vectors. The system can identify the row of the memory for writing data at the current time step as the row with the lowest read counter value.

After identifying a row of the memory, the system writes the latent representation of the current observation to the identified row of the memory. Optionally, the system may also update data previously written to other rows of the memory using the latent representation of the current observation. In particular, each row of the memory may store: (i) a latent representation for a given time step, and (ii) a discounted sum of latent representations for time steps subsequent to the given time step. In this case, in addition to storing the latent representation of the current observation in a respective row of the memory, the system may update each other row the memory by updating the discounted sum of subsequent latent representations stored in each other row of the memory. For example, to write data to the t-th row of the memory, the system may generate a writing weight vector $v_t^{wt}[i] = \delta_{it}$ (where $\delta_{.,.}$ is a Kronecker delta function) and a retroactive memory update vector 84 $_t^{ret}$ as:

$$v_t^{ret} = \gamma v_{t-1}^{ret} + (1-\gamma) v_{t-1}^{wt} \quad (7)$$

where $\gamma$ is a discount factor between 0 and 1, and each of these weight vectors is initialized (i.e., at the first time step) as $v_0^{wt} = v_0^{ret} = 0$. The system may use the weight vectors to update the memory as:

$$M_t = M_{t-1} + v_t^{wt}[z_t, 0]^T + v_t^{ret}[0, z_t]^T \quad (8)$$

where $M_t$ is the 2D matrix representing the updated memory, $M_{t-1}$ represents the non-updated memory, $z_t$ is the latent representation of the current observation, and 0 is a zero-vector of length given by the dimensionality of the latent representation.

The system uses the latent representation of the current observation to generate: (i) a predicted return that will be received by the agent as a result of interactions with the environment after the current observation is received, and (ii) a predicted reconstruction of the current observation (412). In particular, the system processes an input including the latent representation of the current observation using a decoding system, in accordance with current values of decoding system parameters, to generate the predicted return and the predicted reconstruction.

The predicted return may be, for example, a state-value or a Q-value. A state-value refers to the predicted return as a result of the agent performing actions selected in accordance with the current action selection policy (i.e., as defined by the parameters of the MBP system and the action selection system). A Q-value refers to the predicted return as a result of the agent performing actions selected in accordance with the current action selection policy, given the action performed by the agent at the current time step. To generate the predicted return, the system can process an input including the latent representation of the current observation and one or both of: (i) the action selection policy output used by the agent to select an action to be performed at the current time step, and (ii) a representation of an action performed by the agent at the current time step.

For example, the system can generate a Q-value predicted return using a state-value function neural network and an advantage function neural network. The state-value function network is configured to process the latent representation of the current observation and the action selection policy output used by the agent to select the action to be performed at the current time step to generate a state-value estimate. The advantage function network is configured to process the latent representation of the current observation and a representation of the action performed by the agent at the current time step to generate an advantage estimate. The advantage estimate is an estimate of a difference between the Q-value and the state-value at the current time step. The system can generate the predicted return by summing the state-value estimate and the advantage estimate.

The system can generate the predicted reconstruction of the current observation by generating a respective reconstruction of each component of the current observation. To generate the predicted reconstruction of a given component of the observation, the system may process the encoded representation of the given component using a respective decoding neural network (e.g., convolutional image decoding neural network). The decoding neural network used to generate the reconstruction of the given component may have the same architecture as the encoding neural network used to generate the encoded representation of the given component, except the operations are reversed.

The system adjusts the current values of the system parameters using gradients of a prediction objective function and a divergence objective function with respect to the system parameters (414). The system parameters refer some or all of the parameters of the encoding, representation, memory interface, and decoding systems. Rather than adjusting the system parameters at each time step, the system may adjust the system parameters only in response to determining that an update criterion is satisfied. For example, the update criterion may be that a predetermined number of time steps have elapsed since the last time the system parameters were adjusted. In response to determining that an update criterion is not satisfied, the system can return to step 402.

The prediction objective function is based on, for one or more of the preceding time steps: (i) the difference between the predicted return and the actual return for the time step, and (ii) the difference between the predicted reconstruction and the observation for the time step. For example, the prediction objective function $\mathcal{L}_{pred}$ for a time step may be given by:

$$\mathcal{L}_{pred} = \alpha_{return}\mathcal{L}_{return} 30 \; \alpha_{image}\mathcal{L}_{image} + \alpha_{reward}\mathcal{L}_{reward} + \alpha_{action}\mathcal{L}_{action} + \alpha_{velocity}\mathcal{L}_{velocity} + \alpha_{text}\mathcal{L}_{text} \quad (9)$$

where $\alpha_{return}$, $\alpha_{reward}$, $\alpha_{action}$, $\alpha_{velocity}$, and $\alpha_{text}$ are scalar coefficient values. $\mathcal{L}_{return}$ characterizes the difference between the predicted return and the actual return for the time step. If the predicted return is a Q-value determined using a state-value function neural network and an advantage function neural network, as described with reference to step 412, then $\mathcal{L}_{return}$ may be given by:

$$\mathcal{L}_{return} = 1/2[|V_t - \hat{V}_t|^2 + |R_t - \hat{R}_t|^2] \quad (10)$$

where $\hat{V}_t$ is the estimated state-value, $V_t$ is the actual state-value, $\hat{R}_t$ is the estimated Q-value, and $R_t$ is the actual Q-value. The actual Q-value $R_t$ may be determined as:

$$R_t = \begin{cases} r_t + \gamma r_{t+1} + \gamma^2 r_{t+2} + \cdots + \gamma^{k-t+1}\hat{V}_{k+1}, \text{if } k < T \\ r_t + \gamma r_{t+1} \gamma^2 r_{t+2} + \cdots + \gamma^{T-t} r_T, \text{if } T \leq k \end{cases} \quad (11)$$

where k is the future time step that used as the endpoint for determining the predicted return after time step t, and T represents a time step at which the environment "terminates" (e.g., because the agent finishes a task). $\mathcal{L}_{image}$ characterizes how well the reconstructed image matches the observation image, and may be given by:

$$\mathcal{L}_{image} = \sum_{w=1, h=1, c=1}^{|W|, |H|, |C|} [I_t[w,h,c] \log \hat{I}_t[w,h,c] + (1 - I_t[w,h,c]) \log(1 - \hat{I}_t[w,h,c])] \quad (12)$$

where w, h, and c respectively index the width, height, and channels of the image, $I_t[w, h, c]$ represents the intensity of the image at [w, h, c] and $\hat{I}_t[w, h, c]$ represents the intensity of the reconstructed image at [w, h, c]. $\mathcal{L}_{reward}$ characterizes how accurately the predicted reward from the previous time step matches the actual reward at the previous time step, and may be given by:

$$\mathcal{L}_{reward} = 1/2 |\tau_{t-1} - \hat{\tau}_{t-1}|^2 \quad (13)$$

where $\tau_{t-1}$ is the actual reward at the previous time step and $\hat{\tau}_{t-1}$ is the predicted reward at the previous time step. $\mathcal{L}_{action}$ characterizes how accurately the prediction of the action performed at the previous time step matches the action performed at the previous time step, and may be given by:

$$\mathcal{L}_{action} = \sum_{i=1}^{|A|} [a_{t-1}[i] \log(\hat{a}_{t-1}[i]) + (1 - a_{t-1}[i]) \log(1 - \hat{a}_{t-1}[i])] \quad (14)$$

where |A| is the total number of actions that can be performed, $a_{t-1}[i]$ is the i-th component of a one-hot vector representation of the action performed at the previous time step, and $\hat{a}_{t-1}[i]$ is the i-th component of a predicted vector representation of the action performed at the previous time step. $\mathcal{L}_{velocity}$ characterizes how accurately the prediction of the velocity the agent matches the actual velocity of the agent, and may be given by:

$$\mathcal{L}_{velocity} = \frac{1}{2}\sum_{i=1}^{6} |v_t[i] - \hat{v}_t[i]|^2 \quad (15)$$

where $v_t[i]$ is the i-th component of a vector representation of the velocity of the agent, and $\hat{v}_t[i]$ is the i-th component of a predicted vector representation of the velocity of the agent. $\mathcal{L}_{text}$ characterizes how accurately the prediction of a textual instruction provided to the agent matches the actual textual instruction provided to the agent, and may be given by:

$$\mathcal{L}_{text} = \sum_{k=1}^{10} \sum_{i=1}^{1000} [T_t[k,i] \log \hat{T}_t[k,i] + (1 - T_t[k,i]) \log(1 - \hat{T}_t[k,i])] \quad (16)$$

where k indexes the words in the textual instruction (up to 10 words), 1000 is the vocabulary size of possible words, $T_t[k, i]$ has value 1 if the k-th word in the instruction matches the i-th word in the vocabulary and 0 otherwise, and $\hat{T}_t[k, i]$ is the predicted probability that the k-th word in the instruction matches the i-th word in the vocabulary. The overall prediction objective function can be obtained by summing the prediction objective function for one or more time steps.

The divergence objective function is based on, for one or more of the preceding time steps, a measure of similarity between the respective prior and posterior distributions generated at the preceding time step. For example, the divergence objective function $\mathcal{L}_{div}$ for a preceding time step may be given by:

$$\mathcal{L}_{div} = D_{KL}[p|q] \qquad (17)$$

where $D_{KL}[\cdot,\cdot]$ is the Kullback-Leibler divergence measure, p is the prior distribution, and q is the posterior distribution at the time step. The overall divergence objective function can be obtained by summing the divergence objective function for one or more preceding time steps.

The system can determine gradients of the prediction objective function and the divergence objective function using any appropriate technique, for example, backpropagation. The system can use the update rule of any appropriate gradient descent optimization algorithm (e.g., Adam or RMSprop) to adjust the system parameters using the gradients. After adjusting the system parameters, the system can return to step 402.

Figure 5:
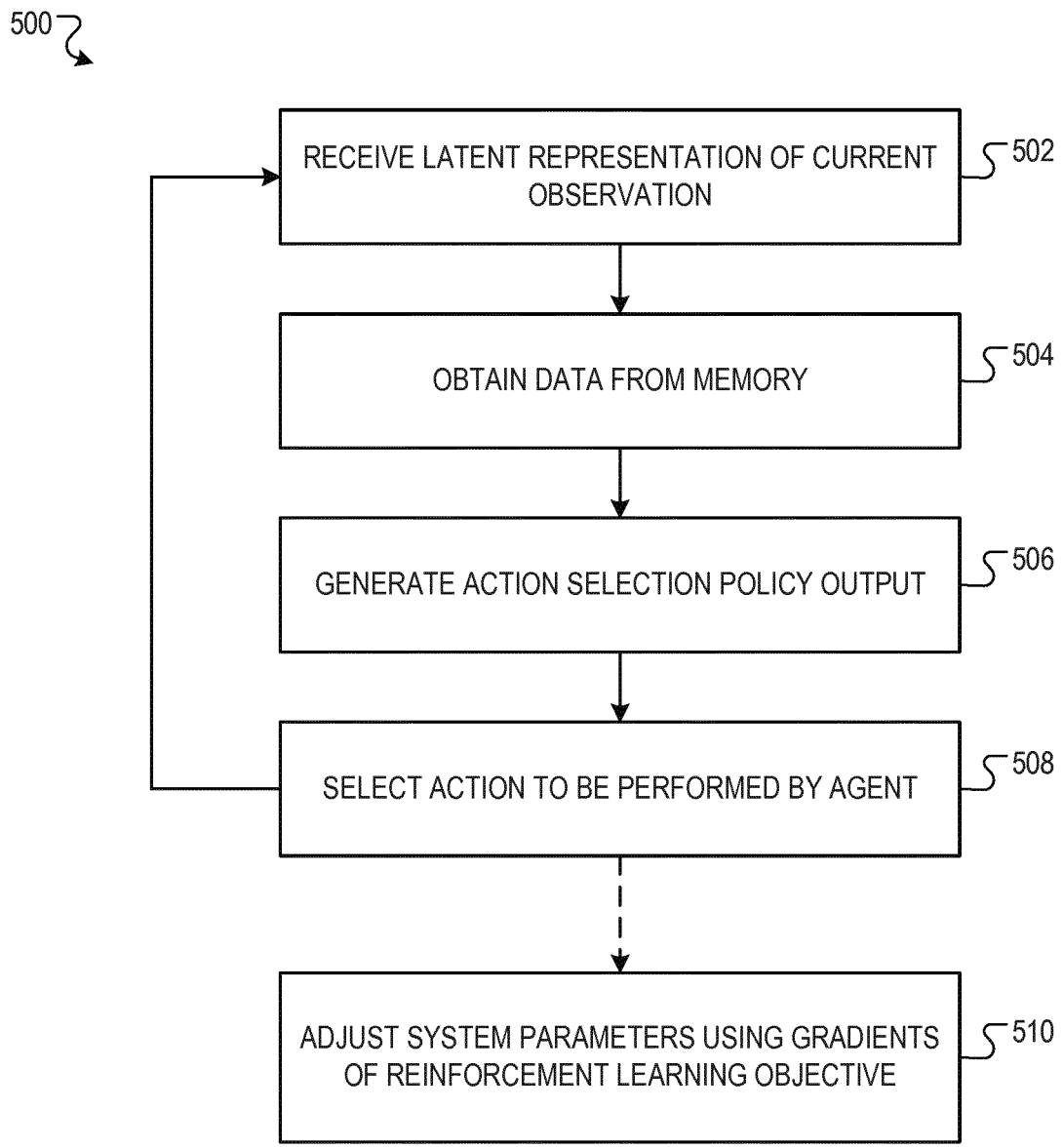
FIG. 5 is a flow diagram of an example process for selecting an action to be performed by an agent using a latent representation generated by a memory-based prediction system.

FIG. 5 is a flow diagram of an example process 500 for selecting an action to be performed by an agent using a latent representation generated by the MBP system. For convenience, the process 500 will be described as being performed by a system of one or more computers located in one or more locations. For example, an action selection system, e.g., the action selection system 104 of FIG. 1, appropriately programmed in accordance with this specification, can perform the process 500.

The system receives a latent representation of the current state of the environment (502). An example process for generating the latent representation of the current state of the environment using an MBP system is described with reference to FIG. 4.

The system obtains data from a memory maintained by the MBP system (504). As described earlier, the memory stores latent representations of previous states of the environment generated at previous time steps. The system may obtain the data read from the memory at the time step by the MBP system. Alternatively, the system may read data directly from the memory in a similar manner as MBP system. More specifically, as described with reference to step 408 of FIG. 4, the system may process the latent representation of the current observation and the data read from the memory at the previous time step using a recurrent neural network to generate a recurrent neural network output. The "recurrent neural network" referred to here is distinct from the recurrent neural network used by the MBP system to read from the memory. The system may process the recurrent neural network output to generate read key vectors, and thereafter use the read key vectors to generate respective readout vectors from the contents of the memory.

The system processes an input including the latent representation of the current state of the environment and the data obtained from the memory using an action selection neural network to generate an action selection policy output (506). If the system reads data directly from the memory using a recurrent neural network, the input processed by the action selection network may additionally include the recurrent neural network output. The policy output may include a respective numerical probability value for each action in a set of possible actions that can be performed by the agent at the time step. The action selection neural network may have any appropriate neural network architecture. For example, the action selection neural network may be a single hidden layer MLP with 200 tanh neurons. The output layer of the action selection network may have the same number of neurons as the number of possible actions that can be performed by the agent.

The system selects the action to be performed by the agent based on the action selection policy output (508). For example, the system may sample an action in accordance with the probability values for the actions specified by the policy output.

During training, the system adjusts the current values of the system parameters using gradients of a reinforcement learning objective function with respect to the system parameters (510). The system parameters refer to some or all of the parameters of the action selection network and optionally, a recurrent neural network used to read data from the memory. Optionally, but not necessarily, the system can adjust the current values of the MBP system parameters using gradients of the reinforcement learning objective function. Rather than adjusting the system parameters at each time step, the system may adjust the system parameters at a time step only in response to determining that an update criterion is satisfied. For example, the update criterion may be that a predetermined number of time steps have elapsed since the last time the system parameters were adjusted. In response to determining that an update criterion is not satisfied, the system can return to step 502.

In one implementation, the gradient of the reinforcement learning objective function may be a "policy gradient" $\Delta\theta$ given by:

$$\Delta\theta = \sum_{t=0}^{T} R_t \nabla_\theta \log \pi_\theta(a_t | h_t)$$

where t indexes time steps, $R_t$ is the return $\tau_t + \tau_{t+1} + \ldots + \tau_T$, and $\nabla_\theta \log \pi_\theta(\alpha_t | h_t)$ is the gradient of the probability value specified by the action selection policy output for the action selected at time step t with respect to the system parameters. A variant of this may include an additional term to increase the entropy of the policy's action distribution.

Figure 6:
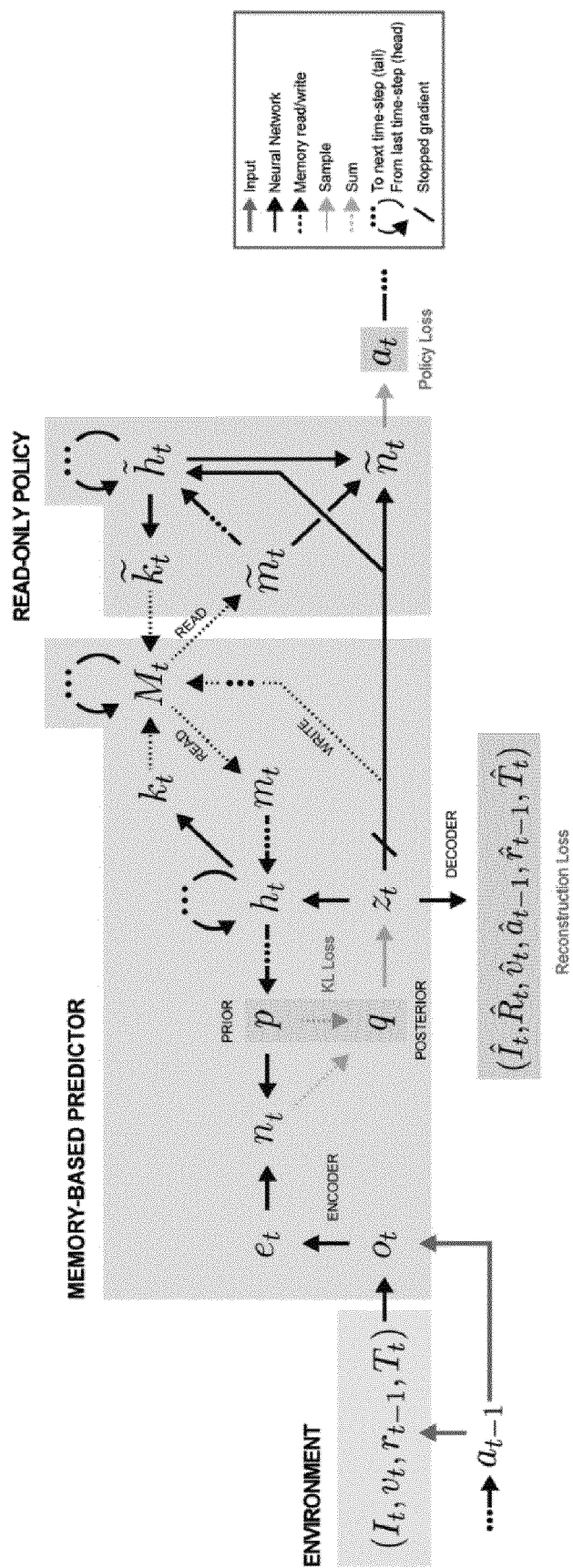
FIG. 6 illustrates operation of an example memory-based prediction (MBP) system and action selection system.

FIG. 6 illustrates the operation of an example memory-based prediction (MBP) system and action selection system as described above. In this example an observation $o_t$ at time t comprising an image $I_t$, an egocentric velocity $v_t$, a previous reward $\tau_{t-1}$ and action $\alpha a_{t-1}$, and optionally a text instruction $T_t$, is encoded to $e_t$ by the encoding system. As previously described a recurrent neural network $h_t$ has produced, e.g. via the prior neural network, a prior p distribution over the latent representation $z_t$ at the previous time step t−1. The mean and log standard deviation of the Gaussian distribution p are concatenated with the embedding $e_t$ and passed through the posterior neural network to form an intermediate variable $n_t$, which is added to the prior to make a Gaussian posterior distribution q, from which the latent representation $z_t$ is sampled. This is inserted into row t of the memory matrix M, represented updated as $M_t$, and passed to the recurrent neural network $h_t$ of the MBP system. The recurrent neural network $h_t$ has multiple read heads each with a key $k_t$ which is used to find matching items $m_t$ in memory. The latent representation $z_t$ is passed as an input to the read-only action selection (policy) neural network (in this example it does not write to the memory), and is also passed through the decoding system, decoder neural networks that produce reconstructed input data (shown with carets) and the predicted return $\hat{R}_t$. The MBP system is trained based on a variational lower bound objective as described above, consisting of a reconstruction loss and a KL divergence between p and q. In the illustrated example the gradient from the policy loss into the MBP system is blocked.

In FIG. 6 the action selection (policy) neural network, by way of example, comprises a recurrent LSTM network $\tilde{h}_t$ which outputs through a neural network, with an intermediate hidden layer $\tilde{n}_t$, for the action probabilities from which an action $\alpha_t$ is sampled and acts on the environment. The recurrent LSTM network $\tilde{h}_t$ has multiple read heads that each produce a key vector $\tilde{k}_t$ that is used to access the data in the memory M in a way similar to that previously described for the MBP system. The read heads return read vectors $\tilde{m}_t$ that are concatenated into $\tilde{n}_t$, and the read data is also provided as an input to the recurrent LSTM network $\tilde{h}_t$.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method for training a memory-based prediction neural network system using a predictive modeling process, wherein the memory-based prediction neural network system includes an encoder and a representation system and has a plurality of memory-based prediction parameters and is configured to:
   receive, by the memory-based prediction neural network system, an observation characterizing a state of an environment interacted with by an agent; and
   process, by the memory-based prediction neural network system, the observation and data read from a memory to update data stored in the memory and to generate a latent representation of the state of the environment;
   the method comprising:
   performing, by the memory-based prediction neural network system, for each of a plurality of time steps:
      receiving a current observation for the time step characterizing a current state of the environment being interacted with by the agent at the time step;
      obtaining the data read from the memory, comprising:
         processing one or more latent representations generated at a previous time step in accordance with current values of the memory-based prediction parameters to generate one or more read keys; and
         generating one or more readout vectors based on a first measure of similarity between: (i) the one or more read keys derived from the one or more latent representations generated at the previous time step, and (ii) data stored in the memory,
         wherein the one or more readout vectors define the data read from the memory;
      processing the current observation for the time step and data read from the memory in accordance with the current values of the memory-based prediction parameters to: (i) update the data stored in the memory, and (ii) generate a latent representation of the current state of the environment as of the time step, comprising:

processing the current observation using the encoder and in accordance with the current values of the memory-based prediction parameters to generate an encoded representation of the current observation;

processing: (i) the encoded representation of the current observation, and (ii) the data read from the memory, using the representation system and in accordance with the current values of the memory-based prediction parameters, to generate the latent representation of the current state of the environment as of the time step; and writing the latent representation of the current state of the environment as of the time step to the memory; and generating, using the latent representation of the current state of the environment as of the time step and in accordance with the current values of the memory-based prediction parameters, data characterizing a predicted return, wherein the predicted return is a prediction for a cumulative measure of rewards that will be received by the agent as a result of interactions with the environment to perform a task after the current observation for the time step is received;

determining, for one or more of the time steps, an actual return for the time step that is a cumulative measure of rewards received by the agent as a result of interactions with the environment to perform the task after the current observation for the time step is received;

determining a gradient based at least in part on, for one or more of the time steps, an error between: (i) the data characterizing the predicted return for the time step, and (ii) the actual return for the time step; and adjusting the current values of the memory-based prediction parameters using the gradient.

2. The method of claim 1, wherein the current values of the memory-based prediction parameters include current values of the representation system parameters and wherein adjusting the current values of the memory-based prediction parameters using the gradient comprises:

adjusting the current values of the representation system parameters using the gradient.

3. The method of claim 1, wherein for each of the plurality of time steps, processing the one or more previous latent representations using the memory-based prediction neural network system and in accordance with the current values of the memory-based prediction parameters to generate the one or more read keys comprises:

processing, using a recurrent neural network and in accordance with current values of recurrent neural network parameters, an input comprising the one or more previous latent representations to generate a recurrent neural network output; and generating the one or more read keys based on the recurrent neural network output.

4. The method of claim 3, wherein processing: (i) the encoded representation of the current observation, and (ii) the data read from the memory, using the representation system and in accordance with the current values of the memory-based prediction parameters, to generate the latent representation of the current state of the environment as of the time step comprises:

processing, using a prior neural network and in accordance with current values of a set of neural network parameters of the prior neural network, an input comprising: (i) the recurrent neural network output, and (ii) the data read from the memory, to generate parameters of a prior probability distribution over a latent representation space;

processing, using a posterior neural network and in accordance with current values of posterior neural network parameters, an input comprising: (i) the parameters of the prior probability distribution, (ii) the encoded representation of the current observation, (iii) the recurrent neural network output, and (iv) the data read from the memory, to generate parameters of a posterior probability distribution over the latent representation space; and generating the latent representation of the current state of the environment as of the time step by sampling a latent representation from the posterior probability distribution.

5. The method of claim 4, wherein:

the parameters of the prior probability distribution include prior mean parameters and prior standard deviation parameters;

the parameters of the posterior probability distribution include posterior mean parameters and posterior standard deviation parameters; and sampling a latent representation from the posterior probability distribution comprises sampling a latent representation from a Normal distribution defined by the parameters of the posterior probability distribution.

6. The method of claim 4, further comprising:

determining a divergence gradient based on, for one or more of the time steps, a second measure of similarity between: (i) the prior probability distribution over the latent representation space at the time step, and (ii) the posterior probability distribution over the latent representation space at the time step; and adjusting the current values of the memory-based prediction parameters using the divergence gradient.

7. The method of claim 1, wherein writing data to the memory using the latent representation of the current state of the environment as of the time step comprises writing the latent representation of the current state of the environment as of the time step to a specific location in the memory and updating, using the latent representation of the current state of the environment as of the time step, data written to the memory at previous time steps.

8. The method of claim 1, wherein writing data to the memory using the latent representation of the current state of the environment as of the time step comprises, in response to determining that the memory is full, overwriting specific data in the memory based on how frequently the specific data is read from the memory.

9. The method of claim 1, wherein the current values of the memory-based prediction parameters include current values of encoding system parameters and wherein adjusting the current values of the memory-based prediction parameters using the gradient comprises:

adjusting the current values of the encoding system parameters using the gradient.

10. The method of claim 1, wherein for each of the plurality of time steps, generating, using the latent representation of the current state of the environment as of the time step and in accordance with the current values of the memory-based prediction parameters, data characterizing the predicted return that will be received by the agent as a result of interactions with the environment after the observation for the time step is received, comprises:

processing, using a decoding system and in accordance with current values of decoding system parameters, a decoding system input to generate the data characterizing the predicted return, wherein the decoding system input comprises: (i) the latent representation of the current state of the environment as of the time step, and (ii) an action selection policy output used by the agent to select an action to be performed at the time step, an action performed by the agent at the time step, or both.

11. The method of claim 10, wherein for each of the plurality of time steps, the decoding system further generates a predicted reconstruction of the current observation for the time step.

12. The method of claim 11, further comprising:
determining an additional gradient based on, for one or more of the time steps, a difference between: (i) the predicted reconstruction of the current observation for the time step, and (ii) the current observation for the time step; and
adjusting the current values of the memory-based prediction parameters using the additional gradient.

13. The method of claim 10, wherein processing, using the decoding system, the decoding system input to generate the data characterizing the predicted return comprises:
processing, using a state-value function neural network and in accordance with current values of state-value function neural network parameters, an input comprising: (i) the latent representation of the current state of the environment as of the time step, and (ii) the action selection policy output used by the agent to select the action to be performed at the time step, to generate a state-value estimate;
processing, using an advantage function neural network and in accordance with current values of advantage function neural network parameters, an input comprising: (i) the latent representation of the current state of the environment as of the time step, and (ii) the action performed by the agent at the time step, to generate an advantage estimate; and
generating the data characterizing the predicted return based on the state-value estimate and the advantage estimate.

14. The method of claim 10, wherein the action selection policy output used by the agent to select an action to be performed at the time step comprises a score distribution over a predetermined set of actions.

15. A real-world system comprising one or more processors and one or more storage devices storing instructions that when executed by the one or more processors cause the one or more processors to perform operations for training a memory-based prediction neural network system using a predictive modeling process, wherein the memory-based prediction neural network system includes an encoder and a representation system and has a plurality of memory-based prediction parameters and is configured to:
receive, by the memory-based prediction neural network system, an input observation characterizing a state of an environment interacted with by an agent; and
process, by the memory-based prediction neural network system, the input observation and data read from a memory to update data stored in the memory and to generate a latent representation of the state of the environment;
the operations comprising:
performing, by the memory-based prediction neural network system, for each of a plurality of time steps:
receiving a current observation for the time step characterizing a current state of the environment being interacted with by the agent at the time step;
obtaining the data read from the memory, comprising:
processing one or more latent representations generated at a previous time step in accordance with current values of the memory-based prediction parameters to generate one or more read keys; and
generating one or more readout vectors based on a first measure of similarity between: (i) the one or more read keys derived from the one or more latent representations generated at the previous time step, and (ii) data stored in the memory, wherein the one or more readout vectors define the data read from the memory;
processing the current observation for the time step and data read from the memory in accordance with the current values of the memory-based prediction parameters to: (i) update the data stored in the memory, and (ii) generate a latent representation of the current state of the environment as of the time step, comprising:
processing the current observation using the encoder and in accordance with the current values of the memory-based prediction parameters to generate an encoded representation of the current observation;
processing: (i) the encoded representation of the current observation, and (ii) the data read from the memory, using the representation system and in accordance with the current values of the memory-based prediction parameters, to generate the latent representation of the current state of the environment as of the time step; and
writing the latent representation of the current state of the environment as of the time step to the memory; and
generating, using the latent representation of the current state of the environment as of the time step and in accordance with the current values of the memory-based prediction parameters, data characterizing a predicted return, wherein the predicted return is a prediction for a cumulative measure of rewards that will be received by the agent as a result of interactions with the environment to perform a task after the current observation for the time step is received;
determining, for one or more of the time steps, an actual return for the time step that is a cumulative measure of rewards received by the agent as a result of interactions with the environment to perform the task after the current observation for the time step is received;
determining a gradient based at least in part on, for one or more of the time steps, an error between: (i) the data characterizing the predicted return for the time step, and (ii) the actual return for the time step; and
adjusting the current values of the memory-based prediction parameters using the gradient.

16. One or more non-transitory computer storage media storing instructions that when executed by one or more processors cause the one or more processors to perform operations for training a memory-based prediction neural network system using a predictive modeling process, wherein the memory-based prediction neural network system includes an encoder and a representation system and has a plurality of memory-based prediction parameters and is configured to:

receive, by the memory-based prediction neural network system, an input observation characterizing a state of an environment interacted with by an agent; and process, by the memory-based prediction neural network system, the input observation and data read from a memory to update data stored in the memory and to generate a latent representation of the state of the environment;

the operations comprising:

performing, by the memory-based prediction neural network system, for each of a plurality of time steps:
  receiving a current observation for the time step characterizing a current state of the environment being interacted with by the agent at the time step;
  obtaining the data read from the memory, comprising:
    processing one or more latent representations generated at a previous time step in accordance with current values of the memory-based prediction parameters to generate one or more read keys; and
    generating one or more readout vectors based on a first measure of similarity between: (i) the one or more read keys derived from the one or more latent representations generated at the previous time step, and (ii) data stored in the memory, wherein the one or more readout vectors define the data read from the memory;
  processing the current observation for the time step and data read from the memory in accordance with the current values of the memory-based prediction parameters to: (i) update the data stored in the memory, and (ii) generate a latent representation of the current state of the environment as of the time step, comprising:
    processing the current observation using the encoder and in accordance with the current values of the memory-based prediction parameters to generate an encoded representation of the current observation;
    processing: (i) the encoded representation of the current observation, and (ii) the data read from the memory, using the representation system and in accordance with the current values of the memory-based prediction parameters, to generate the latent representation of the current state of the environment as of the time step; and
    writing the latent representation of the current state of the environment as of the time step to the memory; and
  generating, using the latent representation of the current state of the environment as of the time step and in accordance with the current values of the memory-based prediction parameters, data characterizing a predicted return, wherein the predicted return is a prediction for a cumulative measure of rewards that will be received by the agent as a result of interactions with the environment to perform a task after the current observation for the time step is received;

determining, for one or more of the time steps, an actual return for the time step that is a cumulative measure of rewards received by the agent as a result of interactions with the environment to perform the task after the current observation for the time step is received;

determining a gradient based at least in part on, for one or more of the time steps, an error between: (i) the data characterizing the predicted return for the time step, and (ii) the actual return for the time step; and adjusting the current values of the memory-based prediction parameters using the gradient.

17. The non-transitory computer storage media of claim 16, wherein the current values of the memory-based prediction parameters include current values of the representation system parameters and wherein adjusting the current values of the memory-based prediction parameters using the gradient comprises:
  adjusting the current values of the representation system parameters using the gradient.

18. The non-transitory computer storage media of claim 16, wherein for each of the plurality of time steps, processing the one or more previous latent representations using the memory-based prediction neural network system and in accordance with the current values of the memory-based prediction parameters to generate the one or more read keys comprises:
  processing, using a recurrent neural network and in accordance with current values of recurrent neural network parameters, an input comprising the one or more previous latent representations to generate a recurrent neural network output; and
  generating the one or more read keys based on the recurrent neural network output.

19. The non-transitory computer storage media of claim 16, wherein writing data to the memory using the latent representation of the current state of the environment as of the time step comprises writing the latent representation of the current state of the environment as of the time step to a specific location in the memory and updating, using the latent representation of the current state of the environment as of the time step, data written to the memory at previous time steps.

20. The non-transitory computer storage media of claim 16, wherein writing data to the memory using the latent representation of the current state of the environment as of the time step comprises, in response to determining that the memory is full, overwriting specific data in the memory based on how frequently the specific data is read from the memory.

* * * * *